US010639528B2

(12) United States Patent
Stefanyshyn et al.

(10) Patent No.: US 10,639,528 B2
(45) Date of Patent: May 5, 2020

(54) METHOD AND SYSTEM FOR MATCHING ATHLETES WITH EQUIPMENT

(71) Applicant: Sport Insight Inc., Calgary (CA)

(72) Inventors: Darren J. Stefanyshyn, Calgary (CA); John W. Wannop, Calgary (CA); Ryan M. J. Madden, Calgary (CA); Jay Tofin Worobets, Calgary (CA)

(73) Assignee: SPORT INSIGHT INC., Calgary, Alberta (CA)

( * ) Notice: Subject to any disclaimer, the term of this patent is extended or adjusted under 35 U.S.C. 154(b) by 523 days.

(21) Appl. No.: 15/351,138

(22) Filed: Nov. 14, 2016

(65) Prior Publication Data

US 2017/0136326 A1    May 18, 2017

Related U.S. Application Data

(60) Provisional application No. 62/255,204, filed on Nov. 13, 2015.

(51) Int. Cl.

| | |
|---|---|
| *A63B 59/70* | (2015.01) |
| *G06Q 10/06* | (2012.01) |
| *G06F 17/40* | (2006.01) |
| *G06Q 50/00* | (2012.01) |
| *G06F 19/00* | (2018.01) |
| *A63B 69/36* | (2006.01) |
| *G06F 30/00* | (2020.01) |

(52) U.S. Cl.
CPC .............. *A63B 59/70* (2015.10); *G06F 17/40* (2013.01); *G06Q 10/0639* (2013.01); *G06Q 50/00* (2013.01); *A63B 2069/3605* (2013.01); *G06F 19/3481* (2013.01); *G06F 30/00* (2020.01)

(58) Field of Classification Search
None
See application file for complete search history.

(56) References Cited

U.S. PATENT DOCUMENTS

| 8,864,598 B2 | 10/2014 | Worobets et al. |
| 2003/0017882 A1* | 1/2003 | Hossack ............ A63B 69/0024 473/222 |
| 2015/0057111 A1* | 2/2015 | Tremblay-Munger ...................... A63B 69/0026 473/446 |

OTHER PUBLICATIONS

Frayne et al. "Improving ice hockey slap shot analysis using three-dimensional optical motion capture: A pilot study determining the effects of a novel grip tape on slap shot performance" J Sports Engineering and Technology 2015 vol. 229(2) 136-144 (Year: 2015).*

(Continued)

*Primary Examiner* — Roy Y Yi
(74) *Attorney, Agent, or Firm* — Stephen M. De Klerk

(57) ABSTRACT

A method and system for matching an athlete with a selected striking tool. The method includes, and the system facilitates, receiving test data resulting from the athlete hitting a test target with a test striking tool to launch the test target. The test data is mathematically transformed to calculate a test functional group score. The test functional group score is compared with a database to match the test functional group score with matched previous data having a similar functional group score to the test functional group score. A selection parameter of the selected striking tool is defined to correspond with a value of the selection parameter associated with a strong performance metric in the matched previous data.

21 Claims, 13 Drawing Sheets

(56) References Cited

OTHER PUBLICATIONS

"Methods for in-field user calibration of an inertial measurement unit without external equipment" Fong et al. Meas. Sci. Technology 19 085202, 2008 (Year: 2008).*
Grover., et al., "The Effect of Hockey Stick Stiffness and Energy Transfer on Puck Velocity for Wrist and Slap Shots", Journal of Undergraduate Research in Alberta, 2013, vol. 3 (1).
Worobets., et al., "The Influence of Shaft Stiffness on Potential Energy and Puck Speed During Wrist and Slap Shots in Ice Hockey", Sport Engineering, Dec. 2006, vol. 9 (4), pp. 191-200.

* cited by examiner

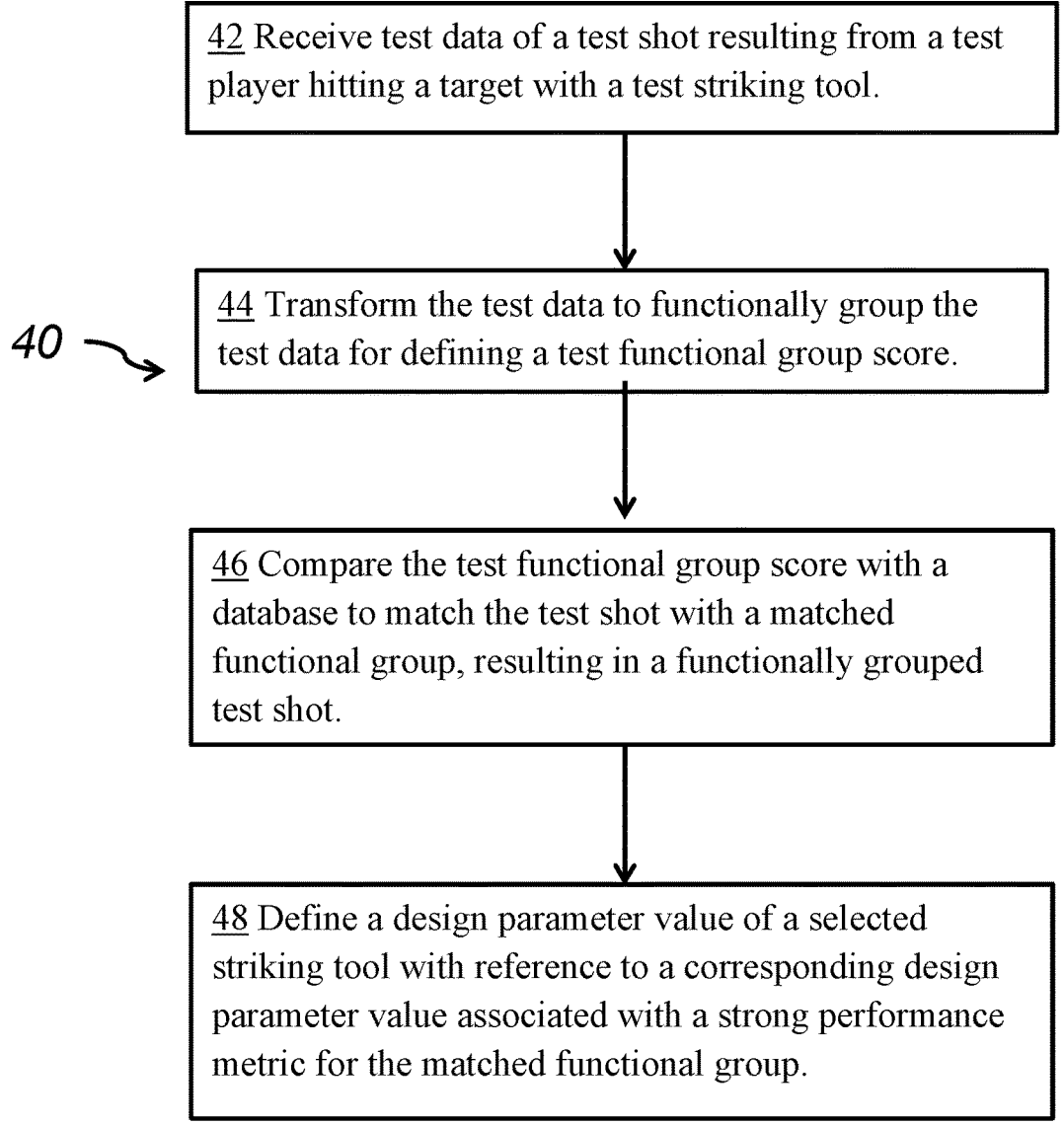

42 Receive test data of a test shot resulting from a test player hitting a target with a test striking tool.

40

44 Transform the test data to functionally group the test data for defining a test functional group score.

46 Compare the test functional group score with a database to match the test shot with a matched functional group, resulting in a functionally grouped test shot.

48 Define a design parameter value of a selected striking tool with reference to a corresponding design parameter value associated with a strong performance metric for the matched functional group.

```
┌─────────────────────────────────────────────┐
│ 142 Receive test data of a test shot resulting from a test │
│ player hitting a puck with a test hockey stick.            │
└─────────────────────────────────────────────┘
                     ↓
┌─────────────────────────────────────────────┐
│ 144 Transform the test data into principle component      │
│ space for defining a test principle component score.       │
└─────────────────────────────────────────────┘
                     ↓
┌─────────────────────────────────────────────┐
│ 146 Compare the test principle component score with a     │
│ database to match the test shot with a matched             │
│ functional group based on similarities between the test    │
│ principle component score and corresponding principle      │
│ component scores in the matched functional group,          │
│ resulting in a functionally grouped test shot.             │
└─────────────────────────────────────────────┘
                     ↓
┌─────────────────────────────────────────────┐
│ 148 Define a design parameter value of a selected         │
│ hockey stick with reference to a corresponding design      │
│ parameter value associated with a strong performance       │
│ metric for the matched functional group in the             │
│ database.                                                  │
└─────────────────────────────────────────────┘
```

FIG. 7

METHOD AND SYSTEM FOR MATCHING ATHLETES WITH EQUIPMENT

CROSS-REFERENCE TO RELATED APPLICATIONS

This application claims the benefit of priority of U.S. Provisional Patent Application No. 62/255,204, filed Nov. 13, 2015, which is hereby incorporated by reference.

FIELD

The present disclosure relates to matching an athlete with equipment used for striking and launching a ball, puck, or similar target.

BACKGROUND

Many sports involve striking and launching a ball, puck or similar target object with a club, racket, hockey stick, or other piece of equipment. Construction of such equipment has changed and evolved over the years. Two important areas in which advances in hockey stick design have improved performance are blade design and shaft materials. Changes in blade design have increased maneuverability and shooting velocity. Changes in materials, such as use of composite materials, has allowed precise control of stick stiffness, facilitating increased storage and return of elastic energy from the player's motion to the puck.

Hockey is enjoyed by participants of a broad range of ages and skill levels, from beginners to professionals. To meet diverse needs across players, hockey stick manufacturers have developed numerous models of hockey sticks. Models of hockey sticks vary in shaft stiffness, blade pattern (blade curve and lie angle), kick point location, and other parameters. Mechanically, alterations to shaft stiffness affect energy storage and return during a shot, which in turn alters puck velocity. Results of research studies on stick stiffness and puck velocity have shown a trend that athletes generally perform better with a more flexible stick, likely as a result of greater deflection of the stick during the shot. However, the results have been very player-specific and depend on how a particular player applies force to or loads the stick. Different players perform better with different stiffness values (Grover et al. 2013; Worobets et al. 2006).

Striking tools used in other sports have similarly evolved significantly in recent decades with advances in materials and manufacturing techniques.

SUMMARY

It is an object of the present disclosure to obviate or mitigate at least one disadvantage of previous approaches to matching an athlete with equipment for striking and launching or shooting a ball, puck, or other small target object. For simplicity, the methods and systems described herein in the context of hockey and matching an athlete with a hockey stick. However, the methods and systems described herein are more generally applicable to other sports or activities in which a tool is used to strike and launch a target (e.g. tennis, badminton, table tennis, baseball, golf, lacrosse, etc.).

Previous approaches to matching an athlete with a hockey stick defined variables that are proxies for strong shot performance. The variables include puck velocity, transfer and return of energy, contact time between the blade and the puck, and accuracy. The variables facilitate matching a player with a hockey stick according to design parameters of the hockey stick including shaft stiffness, blade curve, and lie angle of the stick, or a combination of these features, based on strong performance on one variable, or on multiple variables considered separately. However, interplay between the defined variables also determines performance and the degree and importance of interplay between the variables varies among individual athletes. It is, therefore, desirable to provide a process for matching an athlete with striking equipment that takes into account multiple defined variables and the interplay between the defined variables in a given individual.

Herein provided are methods and systems for matching an athlete with equipment for striking a target to launch the test target, such as a hockey stick for striking a puck. In the case of matching a hockey stick, a test player may be matched with a hockey stick having particular design parameters based on the test player's shot characteristics to facilitate optimizing the test player's shot velocity, accuracy, or other performance metric. The test player takes a test shot by hitting a test puck with a test hockey stick. Sensors receive test data during the test shot. The sensors may be located on the hockey stick, on the puck, or may be external to both the hockey stick and puck. The test data may be functionally grouped to classify the test shot with reference to a database.

The database includes data of the same or comparable type to that which is recorded during the test shot. The database includes data of one or more strong performance metrics, such as puck velocity, accuracy, transfer and return of energy, contact time between the blade and the puck, impulse, or peak force. The database includes data of strong performance metrics with different hockey sticks varying in the value of at least one design parameter of the respective sticks. The database may include data of shots from a large sample of previous players each shooting with one or more sticks having defined design parameters. The design parameters of the hockey stick may include shaft stiffness, blade pattern (blade curve and lie angle), kick point location, and other parameters.

The data in the database may define functional groups into which previous shots are classified based on data associated with the previous shots. The test shot is mathematically transformed and matched with one or more of the functional groups. Each of the one or more functional groups matched with the test shot may be an indicator that a particular design parameter of the stick will improve the value of the strong performance metric for the player taking the test shot. Based on which of the one or more of the functional groups are matched with the test shot, one or more design parameters of a stick may be matched to the test player as likely to result in an improvement in a strong performance metric.

Mathematically transforming the test shot data may include principal component analysis and the test data may be transformed into a multi-dimensional principal component space for comparison with the database. Comparing the test data in principal component space with the database may include application of linear discriminant analysis, neural network analysis, logistic regression analysis, K-means analysis, support vector machine analysis, or any suitable method of analysis. In the principal component space, the test data is compared with the database to locate matching previous data having a similar principal component score to the principal component score of the test data. Based on the similar principal component scores, the test shot is matched with one or more of the functional groups.

In a first aspect, herein provided is a method and system for matching an athlete with a selected striking tool. The method includes, and the system facilitates, receiving test data resulting from the athlete hitting a test target with a test striking tool to launch the test target. The test data is mathematically transformed to calculate a test functional group score. The test functional group score is compared with a database to match the test functional group score with matched previous data having a similar functional group score to the test functional group score. A selection parameter of the selected striking tool is defined to correspond with a value of the selection parameter associated with a strong performance metric in the matched previous data.

In a further aspect, herein provided is a method of matching an athlete with a selected striking tool. The method includes receiving test data resulting from the athlete hitting a target object with a test striking tool for launching the target object; transforming the test data for defining a test functional group score; comparing the test functional group score with a database for matching the test functional group score with matched previous data having a similar functional group score to the test functional group score; and defining a design parameter value of the selected striking tool with reference to a corresponding design parameter value associated with a strong performance metric in the matched previous data.

In some embodiments, transforming the test data comprises transforming the test data into a principal component space defined by the database; the test functional group score comprises a principal component score; comparing the test functional group score with the database comprises comparing the test principal component score with the database in the principal component space; and the matched previous data comprises data having a similar principal component score to the test principal component score. In some embodiments, the method comprises processing at least a portion of the test data to a derived variable and transforming the test data into the principal component space comprises transforming the derived variable.

In some embodiments, the target object comprises a test puck and the test striking tool comprises a test hockey stick. In some embodiments, transforming the test data comprises transforming the test data into a principal component space defined by the database; the test functional group score comprises a principal component score; comparing the test functional group score with the database comprises comparing the test principal component score with the database in the principal component space; and the matched previous data comprises data having a similar principal component score to the test principal component score. In some embodiments, the method comprises processing at least a portion of the test data to a derived variable and transforming the test data into the principal component space comprises transforming the derived variable. In some embodiments, the test data comprises stick deflection data; a shaft of the test hockey stick has a known stiffness value; and processing at least a portion of the test data to the derived variable comprises processing the stick deflection data and the known stiffness value to provide impulse on the puck.

In some embodiments, the target object comprises a test puck and the test striking tool comprises a test hockey stick. In some embodiments, the test data comprises puck velocity, the design parameter comprises shaft stiffness, and the strong performance metric comprises puck velocity.

In some embodiments, the target object comprises a test puck and the test striking tool comprises a test hockey stick. In some embodiments, the test data comprises accuracy data, the design parameter comprises a feature of a blade pattern, and the strong performance metric comprises accuracy. In some embodiments, the accuracy data comprises distance from a target. In some embodiments, the feature comprises a blade curve. In some embodiments, the feature comprises a lie angle.

In some embodiments, the target object comprises a test puck and the test striking tool comprises a test hockey stick. In some embodiments, the principal component comprises stick deflection at release. In some embodiments, receiving test data comprises receiving puck velocity data from an optical sensor. In some embodiments, receiving test data comprises receiving contact data from force sensors on a blade of the hockey stick for detecting contact between the blade and the puck. In some embodiments, receiving test data comprises receiving deflection data from strain sensors on a shaft of the hockey stick for detecting deflection of the shaft. In some embodiments, receiving test data comprises receiving deflection data from optical sensors. In some embodiments, receiving test data comprises receiving contact data from optical sensors. In some embodiments, comparing the test principal component score with the database in the principal component space comprises application of linear discriminant analysis. In some embodiments, comparing the test principal component score with the database in the principal component space comprises application of neural networking analysis. In some embodiments, comparing the test principal component score with the database in the principal component space comprises application of logistic regression analysis. In some embodiments, comparing the test principal component score with the database in the principal component space comprises application of K-means analysis. In some embodiments, comparing the test principal component score with the database in the principal component space comprises application of support vector machine analysis. In some embodiments, the design parameter and the corresponding design parameter each comprises a shaft stiffness value; in some embodiments, the shaft stiffness value is selected from 85 flex, 100 flex, or 110 flex. In some embodiments, the design parameter and the corresponding design parameter each comprises a blade curve. In some embodiments, the design parameter and the corresponding design parameter each comprises a lie angle. In some embodiments, the design parameter and the corresponding design parameter each comprises a kick point. In some embodiments, the strong performance metric in the previous data comprises a high puck velocity. In some embodiments, the strong performance metric in the previous data comprises a high contact time. In some embodiments, the strong performance metric in the previous data comprises a high impulse. In some embodiments, the strong performance metric in the previous data comprises a high stick deflection. In some embodiments, the strong performance metric in the previous data comprises a low stick deflection at puck release.

In a further aspect, herein provided is a system for matching an athlete with a selected striking tool comprising: a data acquisition module for acquiring test data of the athlete hitting a target object with a test striking tool for launching the target object; a computer readable processor in communication with the data acquisition module for receiving the test data and having instructions encoded thereon for receiving the test data; transforming the test data for defining a test functional group score; comparing the test functional group score with a database. The database includes previous test data and at least one defined functional group, for matching the test functional group score with matched previous data in a defined functional group having a similar functional group score to the test functional group score. The instructions include defining a design parameter value of the selected striking tool with reference to a corresponding design parameter value associated with a strong performance metric in the matched previous data. The system includes a computer readable medium in communication with and accessible by the computer readable processor, the computer readable medium having the database stored thereon for access by the computer readable processor.

In some embodiments, the data acquisition module comprises an optical data acquisition module for receiving test data comprising a velocity of the target object.

In some embodiments, the data acquisition module comprises an optical data acquisition module for receiving test data comprising a shaft deflection of the test striking tool. In some embodiments, the data acquisition module comprises optical targets on a shaft of the test striking tool for facilitating receiving the test data comprising the shaft deflection of the test striking tool.

In some embodiments, the data acquisition module comprises force sensors located on a striking surface of the test striking tool for receiving test data of contact and force.

In some embodiments, the data acquisition module comprises conducting material located on a striking surface of the test striking tool and on the target object for receiving test data of contact.

In some embodiments, the data acquisition module comprises strain sensors located on a shaft of the test striking tool for receiving test data of shaft deflection.

In some embodiments, the data acquisition module comprises an inertial sensor located on the target object for receiving test data of target velocity.

In some embodiments, the target object comprises a test puck and the test striking tool comprises a test hockey stick.

In a further aspect, herein provided is a computer readable medium having instructions encoded thereon for receiving test data resulting from an athlete hitting a target object with a test striking tool for launching the target object; transforming the test data for defining a test functional group score; comparing the test functional group score with a database for matching the test functional group score with matched previous data having a similar functional group score to the test functional group score; and defining a design parameter value of the selected striking tool with reference to a corresponding design parameter value associated with a strong performance metric in the matched previous data.

In a further aspect, herein provided is a method of matching an athlete with a selected hockey stick comprising: receiving test data resulting from the athlete hitting a test puck with a test hockey stick for shooting the test puck; transforming the test data for defining a test functional group score; comparing the test functional group score with a database for matching the test functional group score with matched previous data having a similar functional group score to the test functional group score; and defining a design parameter value of the selected hockey stick with reference to a corresponding design parameter value associated with a strong performance metric in the matched previous data.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 6 is a flow chart of a method of matching a test player with equipment having a selected design parameter value associated with a strong performance a database;

FIG. 7 is a flow chart of a method of matching a test player with a hockey stick having a selected design parameter value associated with a strong performance in a database;

DETAILED DESCRIPTION

Figure 1:
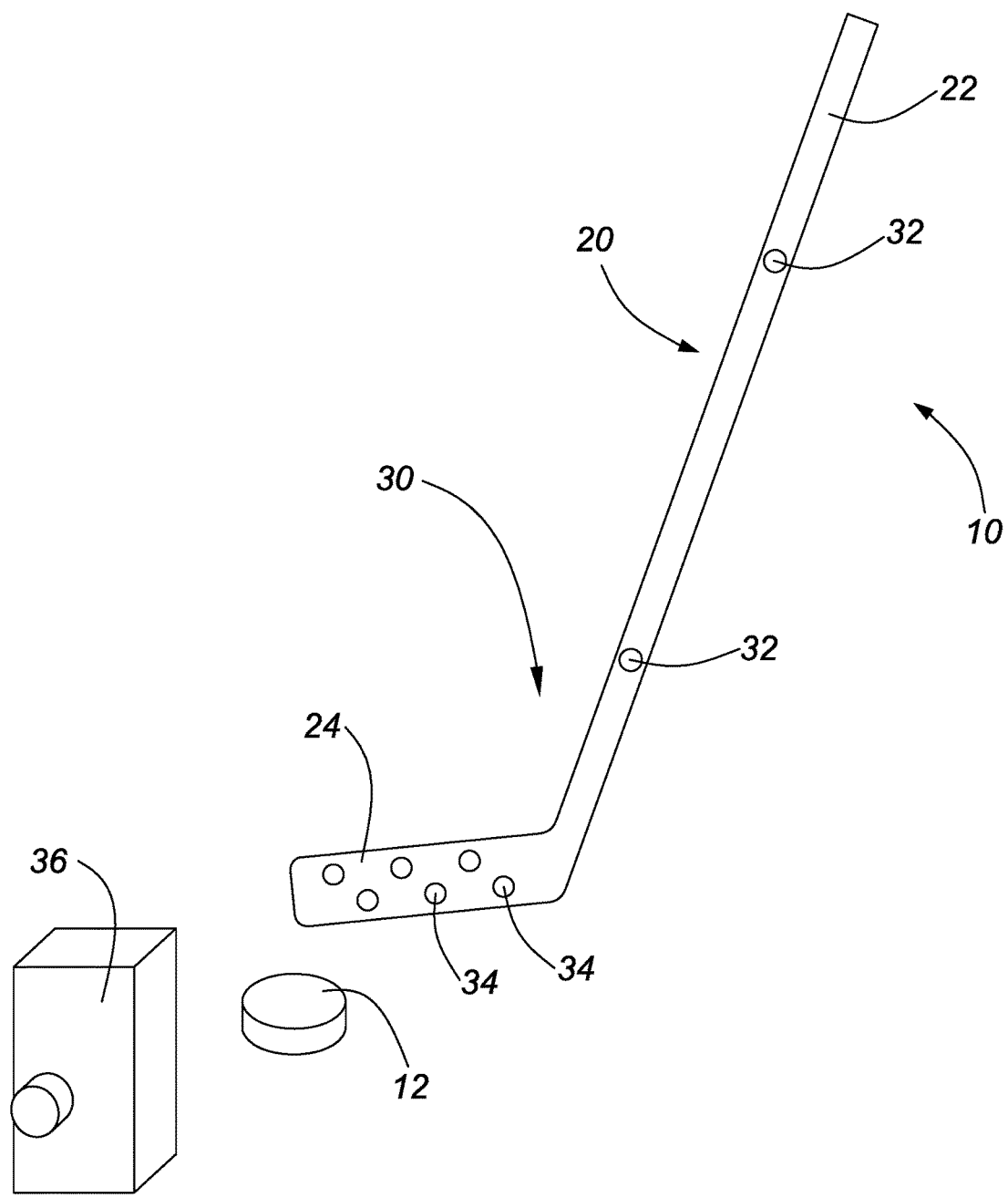
FIG. 1 is a schematic of a data acquisition system for matching an athlete with a hockey stick.

Generally, the present disclosure provides a method and system for matching an athlete with equipment used for striking a ball, puck, or similar object. The particular embodiments described in detail herein apply to hockey specifically but any sport where a striking tool (e.g. a hockey stick, baseball bat, cricket bat, tennis or other racket, etc.) is used to hit an object (e.g. a puck, a ball, a birdie, etc.) could benefit from application of the methods and systems presented herein.

The relationship between stick deflection and puck velocity was used to prepare a previous hockey stick fitting system as detailed in J. T. Worobets, J. C. Fairbairn, and D. J. Stefanyshyn, "The Influence of Shaft Stiffness on Potential Energy and Puck Speed During Wrist and Slap Shots in Ice Hockey", *Sport Engineering* (2006) 9, 191-200. The method of Worobets et al. quantifies strain with strain gauges on the hockey stick shaft. The measured strain is used to calculate deflection. The deflection, puck velocity, and shaft stiffness are used to calculate storage and return of energy. Using puck velocity as a metric for storage and return of energy, Worobets et al. shows that storage and return of energy is affected by stick stiffness. Worobets et al. would facilitate selecting a stick based on defined variables such as deflection, puck velocity, and storage and return of energy.

In R. Grover, B. Wannop, and D. Stefanyshyn, "The Effect of Hockey Stick Stiffness and Energy Transfer on Puck Velocity for Wrist and Slap Shots", *Journal of Undergraduate Research in Alberta*, (2013) 3(1), it is shown that greater blade-puck contact time is associated with increased shot velocity. Blade and puck contact time is not continuous during the shot, with some players having many transient separations of the puck and blade during a single shot. By measuring contact time between the blade and the puck, Grover et al. expanded on the shot characteristics associated with strong performance defined in Worobets et al.

Use of the systems in either of Worobets et al. or Grover et al. can provide data on puck velocity, deflection, and impulse to match a player with a given shaft stiffness or other design parameter of a hockey stick. Each of these previous systems could then be applied to match a player to a shaft stiffness based on the defined variables measured. For each design parameter that a player is considering changing in their stick, a separate shot must be made. For example, if three different hockey sticks with different shaft stiffness values are available, a player must shoot with each of the three sticks to check which stick delivers the greatest value in puck velocity (or any other defined variable selected as a strong performance metric). For example, three different hockey sticks having shaft stiffness values of 85 flex, 100 flex, and 110 flex may be used. In this case, when applying the previous systems of Worobets et al. or Grover et al., the player would have to shoot at least once with each of the three sticks to have the three sticks ranked according to one or more defined performance metrics, such as puck velocity, contact time, maximum deflection, or impulse. The stick resulting in the greatest performance on one or more of the performance metrics would be matched with the player.

The methods and systems described herein, although more generally applicable, will be described with respect to hockey. In the context of hockey, the methods and systems described herein facilitate matching a test player with a selected stick having a value of a design parameter selected to increase a selected performance metric for the test player. The methods and systems described herein allow matching based on a single trial or on an average of multiple trials. Each trial includes data of one or more test shots resulting from the test player hitting a test puck with a test stick. Whether from a single-shot trial or multiple trials, the test player's shot is referred to as a test shot. Defined variables are included in or derived from test data received during the test shot.

The defined variables are mapped against time, mathematically transformed, and compared with a database to define the test shot in terms of one or more functional groups. Previously-acquired data in the database defines functional groups into which previous shots are classified. The previous data used to define functional groups in the database is indicative of features of the previous shots and how previous players in each functional group load the stick. The functional groups allow the test player to be matched with a stick having design parameter values (e.g. shaft stiffness values, blade design, etc.), or combinations of design parameters, associated with strong performance metrics in previous players of the same functional group. The design parameter values are indicative of design parameter values for the hockey stick that may improve a strong performance metric for the test player. The strong performance metric may include puck velocity, accuracy, transfer and return of energy, contact time between the blade and the puck, impulse, or peak force.

The methods and systems described herein may apply any suitable approach to functional grouping (e.g. linear discriminant analysis ("LDA"), neural networking analysis, logistic regression analysis, K-means analysis, support vector machine analysis, etc.). While more broadly applicable, specific examples of the methods and systems described herein apply LDA. When applying LDA in the method and systems described herein, the test player is placed in a class with previous players having similar scores of a principal component, and in some cases of one or more additional components, applicable to the test shot. A test principal component score of the test data is calculated based on transformation of the raw test data into an existing principal component space generated from the database. The transformation may be completed using principal component analysis ("PCA") or any suitable transformation technique. The transformation may be applied to the test data directly, to a derived variable that is derived from the test data, or to both.

Data Acquisition System

FIG. 1 shows a system 10 for practicing methods described herein applied to hockey. Other systems may also be assembled for practicing methods described herein for hockey (e.g. FIGS. 2 to 4), or for other sports or activities that involve striking a target with a striking tool to launch the target (e.g. tennis as shown in FIG. 5). The striking tools of these sports commonly include a shaft (e.g. the shaft 22 of the hockey stick 20 in FIG. 1 or the shaft 422 of the tennis racket 420 in FIG. 5, etc.) and a striking surface (e.g. the blade 24 of the hockey stick 20 in FIG. 1 or the head 424 of the tennis racket 420 in FIG. 5, etc.).

In the system 10, a test hockey stick 20 is used to hit a test puck 12 while data is received by a data acquisition system 30. The test hockey stick 20 includes a shaft 22 and a blade 24. The shaft 22 has a shaft stiffness that is a result of methods and materials used to manufacture the shaft 22. The blade 24 extends from the shaft 22 at a lie angle. The blade 24 curves inward for defining a pocket to cup the puck, providing control during play. The lie angle is between the shaft 22 and the ice when the blade 24 is flat on the ice.

The blade may define a blade pattern that includes definition in terms of the blade curve, the lie angle, or other features. The blade is curved to define the pocket, and the curve may begin at different portions of the blade 24. The blade curve may have a toe curve, a heel curve, or a mid curve. The lie angle is an expression of the angle between the shaft and the ice when the blade is flat on the ice. The lie angle is expressed on a scale of 4 to 8, with 4 being the lowest to the ice (i.e. lower value of the angle between shaft and the ice), and 8 being the highest from the ice (i.e. higher value of the angle between the shaft and the ice). Blade patterns may be associated with professional hockey players and defined by a serial number as shown in Table 1:

TABLE 1

Common blade patterns

| Blade Pattern | Blade Curve | Lie Angle | Toe Contour |
|---|---|---|---|
| Crosby (P87) | Heel | 7 | Round |
| Crosby (P87A) | Mid-Heel | 5.5 | Round |

TABLE 1-continued

Common blade patterns

| Blade Pattern | Blade Curve | Lie Angle | Toe Contour |
|---|---|---|---|
| Bergeron (P46) | Mid | 5.5 | Round |
| Duchene (P42) | Mid-Heel | 5 | Round |
| Hedman (P40) | Center | 5 | Square |
| Datsyuk (P38) | Mid-Heel | 6 | Square |
| Phaneuf P36A (Spezza P36) | Heel | 6 | Round |
| Hamrlik P34 | Mid-Heel | 6 | Round |
| Heatley P9 | Mid | 5 | Round |

Blade patterns used to acquire the data in Examples I and II below are bolded in the above Table 1.

The data acquisition system 30 includes strain gauges 32 on the shaft 22, a plurality of resistive force sensors 34 on the blade 24, and an optical velocity measuring device 36. The strain gauges 32 receive test data of stick deflection. The resistive force sensor 34 receives test data of blade-puck contact time. The amount of energy being transferred from the stick 20 to the test puck 12 due to deflection of the shaft 22 is quantified by calculating the impulse imparted on the test puck 12 using the deflection of the shaft 22 when the blade 24 is in contact with the test puck 12, combined with the stiffness value of the shaft 22. The impulse can be calculated from stick deflection, contact time and stick stiffness values.

The amount of deflection in the shaft 22 during the test shot is measured using the strain gauges 32. The strain gauges 32 may be mechanically calibrated using a cantilever or three-point bend test to determine the amount of linear stick deflection, corresponding to a specific amount of strain in the shaft 22 as measured by the strain gauges 32.

Stick-puck contact time during the test shot is measured with the resistive force sensors 34 on the blade 24. Each force sensor 34 records both time at and during which the test puck 12 is in contact with the blade 24. Where a plurality of force sensors 34 are included on the blade 24, as in the system 10, data of the location of the puck on the blade 24 at different times during the test shot is also received by the force sensors 34. However, a system could also be produced in which a single force sensor is used (not shown).

The contact time between the test puck 12 and the blade 24 is relevant to calculating the effect of recoil of the deflected shaft 22 on the impulse, the transfer of energy, or both, from the test hockey stick 20 to the test puck 12. The impulse that the test hockey stick 20 imparts on the puck is calculated with reference to the stiffness value of the shaft 22 and the amount of deflection during periods of contact with the test puck 12.

The optical velocity measuring device 36 records an image of the test puck 12 travelling through the air after the test shot. The trajectory of the test puck 12 is calculated based on the image. The velocity of the test puck 12 is calculated based on the trajectory of the test puck 12. The optical velocity measuring device 36 may record any suitable image for calculating the trajectory of the test puck 12 (e.g. a single image, a series of images, a video recording, etc.). The optical velocity 36 measuring device may include detection based on radar or other wavelengths that are not within the visible spectrum of the human eye.

The data acquisition system 30 is one example of a data acquisition system. Any suitable data acquisition system may be applied for each of deflection of the shaft 22 (e.g. optical motion capture systems, inertial sensors, magnetic sensors, etc.), contact time between the test puck 12 and the blade 24 (e.g. optical motion capture systems, a circuit system wherein the stick 20 and the 12 puck are coated with a conductive material and when in contact complete an electrical circuit,), and puck velocity (e.g. accelerometers or other inertial sensors on the test puck 12, radar-based speed detection, etc.). In addition, where other features of the test shot are measured, other suitable sensors may be included in a data acquisition system. Examples in the context of hockey other than the system 10 are provided in FIGS. 2 to 4. In addition, FIG. 5 shows with respect to tennis, other sensors may be applied to acquiring the test data.

Figure 2:
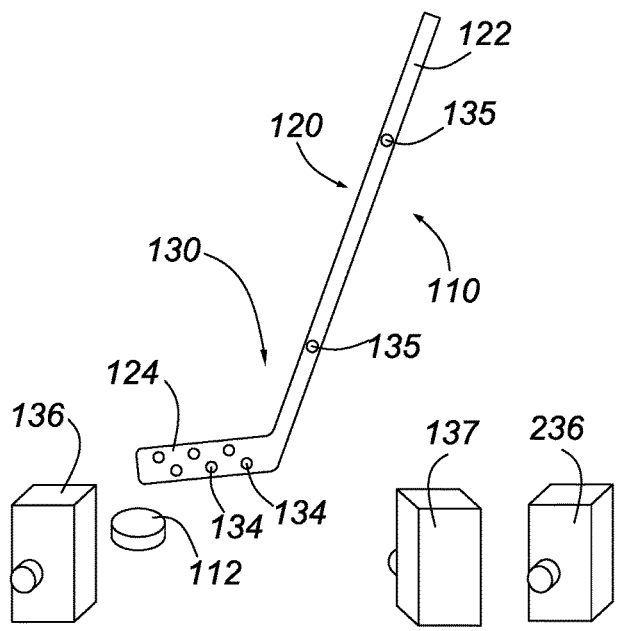
FIG. 2 is a schematic of a data acquisition system for matching an athlete with a hockey stick.

FIG. 2 shows a schematic of a system 110. The system 110 includes many of the components of the system 10. In addition to the optical velocity measuring device 136, the system 110 includes an optical deflection sensor 137 for measuring stick deflection optically during a test shot. The system 110 does not include strain gauges, such as the strain gauges 32 of the system 10. Stick deflection is measured by recording any suitable image for receiving data of stick deflection and determining peak stick deflection and other derived variables based on the stick deflection (e.g. a single image, a series of images, a video recording, etc.). The optical deflection measuring device 137 may include detection based on radar or other wavelengths that are not within the visible spectrum of the human eye. A pair of optical targets 135 are included on the shaft 122 to provide a frame of reference for the optical deflection measuring device 137. The pair of optical targets 135 may be separated by a distance at which shaft deflection can be easily located by the optical deflection measuring device 137, and may wrap around the entire girth of the outside surface of the shaft 122 to provide a frame of reference at any angle between the optical targets 135 and the optical deflection velocity measuring device 137.

Figure 3:
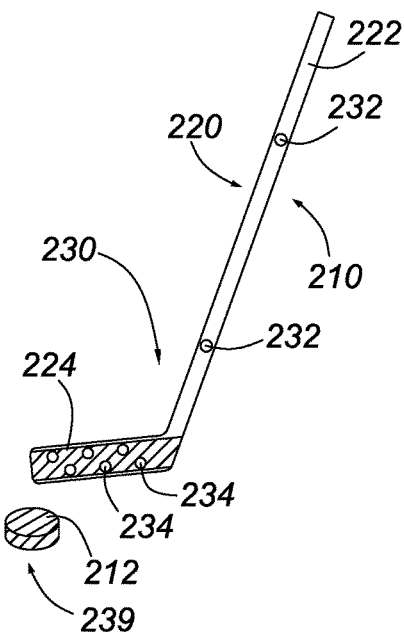
FIG. 3 is a schematic of a data acquisition system for matching an athlete with a hockey stick.

FIG. 3 shows a schematic of a system 210. The system 210 includes many of the components of the system 10. In addition, the system 210 includes blade conductive material 238 on the blade 224 and puck conductive material 239 on the test puck 212. Together, the blade conductive material 238 and the puck conductive material 239 provide the data acquisition system 230 another input for redundant data on contact between the test puck 212 and the blade 224. Alternatively to providing a redundant data source, the blade conductive material 238 and the puck conductive material 239 may free up bandwith on the force sensors 234 to measure a maximum force only.

Figure 4:
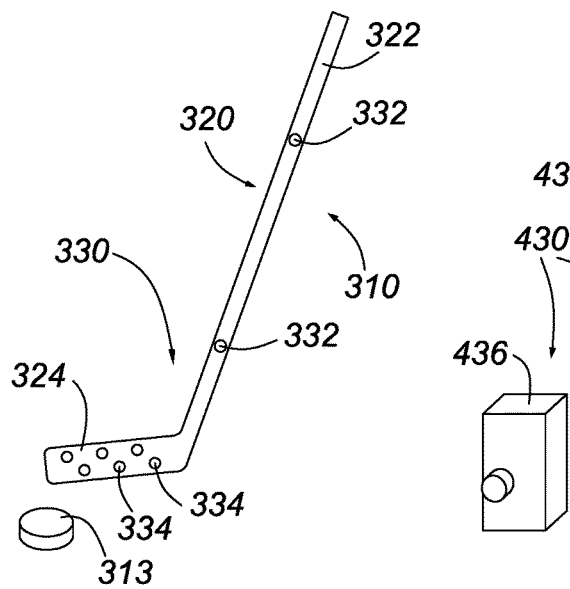
FIG. 4 is a schematic of a data acquisition system for matching an athlete with a hockey stick.
Figure 5:
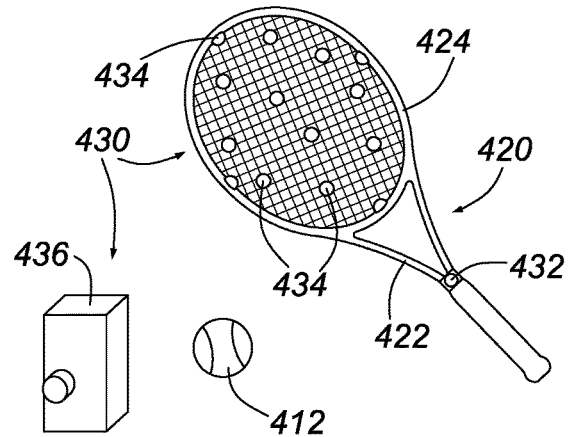
FIG. 5 is a schematic of a data acquisition system for matching an athlete with a tennis racket.

FIG. 4 shows a schematic of a system 310 with an inertial sensor test puck 313. No optical or other speed sensor is required, such as the optical velocity measuring device 36. The inertial sensor test puck 313 may also be included as a redundant system in a system including an optical velocity measuring device, such as the systems 10, 110, or 210. Data may be stored locally on the inertial sensor test puck 313 to mitigate potential interruptions in transmission when the inertial sensor test puck 313 is struck by the test hockey stick 320.

FIG. 5 shows a schematic of a system 410 including a test tennis racket 420 having a shaft 422 and a head 424. A test tennis ball 412 can be struck by the head 424 of the test tennis racket 420. A data acquisition system 430 includes a strain gauge 432 on the shaft 422 and a force sensor 434 on the head 424. An optical velocity measuring device 436 may record the trajectory of the test tennis ball 412 when it is struck by the test tennis racket 420. The system 410 may be put into practice similarly to the system 10 to select different features of a tennis racket for an athlete based on a test swing of the test tennis racket 420 to strike the test tennis ball 412.

Functional Grouping

The systems 10, 110, 210, or corresponding systems differing in data acquisition methods, or a corresponding system using a striking tool other than the test hockey stick 20 (e.g. the test tennis racket 420, etc.), and a target other than the test puck 12 (e.g. the test tennis ball 412), may be applied to practice the methods described herein through functional grouping of test data of a test shot. The functional grouping includes comparing the transformed data with a database, classifying the test shot into one or more functional groups based on the comparison, and matching the player with equipment based on the results of the classification.

FIG. 6 is a flow chart of a method 40 of matching a player with a striking tool by classifying a test shot performed by the player into one or more functional groups. At step 42, the player uses a test striking tool to take a test shot at a test target to launch the test target. Test data of the test shot is acquired. The test data may include data of striking tool deflection, target-tool contact time, maximum target velocity, or any suitable data that can be applied to step 44. Determining initial and final test target contact time and aligning the timelines of the various types of data may also take place at step 42. In addition to data that is directly measured, derived data may also be calculated as part of step 42. Examples of derived data include impulse (using deflection, stiffness of the striking tool, and target-tool contact time), peak deflection, and deflection at release.

At step 44, the test data is mathematically transformed to functionally group the test data and define a test functional group score of the test shot. Transforming the test data to define a test functional group score may result in data reduction and an indication of which variables contribute to the variability in the test data and to what extent. The test functional group score will be determined by one or more variables in the test data, such as striking tool deflection, target-tool contact time, maximum target velocity, impulse, peak deflection, deflection at release, or any suitable variable.

At step 46, the test functional group score is compared with a database to match the test functional group score with data of previous shots having a similar functional group score to the test shot. The comparison may be with a classifier algorithm that identifies a combination of variables that define, and distinguish between, two or more functional groups. The database includes data of the same or a similar type as, or which is otherwise suitable for comparison to, the test data acquired during the test shot. The database also includes functional groups defined by classification of the data. The comparison provides a functionally grouped test shot, which is associated with one or more functional groups defined in the database.

The database may be used to match the test shot with one of the functional groups based on either a single test shot or on multiple test shots. The test shot may be matched to a functional group, and a design parameter for a striking tool selected, after a single shot and without the test player having to take a shot with different striking tools, different shot techniques, or a combination of both. Where multiple test shots are applied, the test shots may be under identical conditions to be averaged or otherwise normalized for providing a single test data set. Alternatively, the test shots may be made under a variety of conditions in terms of either the player's shot technique, design features of the striking tool, design features of the target, or other variables. In applications with multiple test shots, generally the more test shots that are included, whether with constant or altered variables, the greater fit would be expected for the test functional group score with the database. However, there would be a point of diminishing returns after which additional repeats of a shot under selected conditions, or additional shots under different conditions, will not improve the quality of the fit.

At step 48, a design parameter value is defined for a selected striking tool expected to improve a strong performance metric of the player based on the test shot. The design parameter value is defined with reference to a corresponding design parameter value associated with a strong performance metric value for the matched functional group in the database.

In addition to being used to match the test player with a striking tool, the test data may also be added to the database for expanding the database. Expanding the database may include the test player taking multiple shots under consistent or varied conditions, and otherwise in accordance with the scope of data used in the database. The conditions may include different techniques for the shots, altered parameters in the test striking tool, or other conditions. The additional empirical data may improve the database by adding a greater amount of data to the database and providing further definition of the functional groups defined in the database. However, once the database includes a sufficient number of player shot samples to provide a meaningful reference point for matching a player with a striking tool based on future shot data, the database may be used to match the test player with a striking tool having a design parameter associated with a strong performance metric in the functional group with which the test shot is matched.

Linear Discriminant Analysis for Matching a Hockey Stick

FIG. 7 is a flow chart of a method 140 of matching a player with a hockey stick by classifying a test shot performed by the player with functional grouping based on PCA and LDA. At step 142, the player uses a test hockey stick to take a test shot at a test puck to launch the test puck. Test data of the test shot is acquired. The test data may include data of stick deflection, puck-stick contact time, maximum puck velocity, or any suitable data that can be applied to step 144. Determining initial and final puck contact time and aligning the deflection and contact timelines may also take place at step 142. Derived variables such as impulse (using deflection, stick stiffness and puck-blade contact time), peak stick deflection, and stick deflection at release may also be calculated as part of step 142.

At step 144, the test data is transformed (e.g. by PCA, etc.) into principal component space to calculate a test principal component score of the test shot. The principal component space is defined by the database of step 146. The test principal component score will be determined by one or more variables in the test data, such as hockey stick deflection, puck-stick contact time, maximum puck velocity, impulse, peak stick deflection, and stick deflection at release, or any suitable variable. The test principal component score will also be determined by various relationships between the variables in the test data. While the test principal component score may be determined as a result of many variables and the interactions between those variables, the deflection, impulse, impulse after peak deflection, and deflection at puck release are each often major drivers of the resulting principal component score.

At step 146, the test principal component score is compared with the database to match the test principal component score with data of previous shots having a similar principal component score. Once the test principal component score is matched with the data of previous shots in the database, the test shot may be matched with one or more matched functional groups, providing a functionally grouped test shot. In most cases, more than one test principal component score of the test shot will be calculated to account for a sufficiently large amount of variability in the database to provide a reasonable confidence level in the comparison at step 146. For example, in some cases 12 to 14 principal components will account for 90 to 95% of the variability in the database, and a principal component score for each of these 12 to 14 principal components will be calculated and compared to the database in principal component space.

The data of previous shots included in the database is also transformed or transformable into the principal component space, allowing comparison of the test principal component score with the previous data in principal component space. The test principal component score may be compared with the database by passing the test principal component score into a classification algorithm trained by the database. The algorithm may be trained by the database based on relationships between variables in the previous shot data that have high variability between shots under different circumstances. Similarly, the relationships between the variables in the test data that provide the test principal component score may be defined with reference to the high-variability features of the data of previous shots included in the database.

In addition to previous shot data of the same or a similar nature as the test shot data, the database includes identified functional groups within the previous shot data. The functional groups included in the database also include principal components identified for the functional groups. After transformation of the test data into the principal component space, a classifier algorithm (e.g. LDA, neural networking analysis, logistic regression analysis, K-means analysis, support vector machine analysis, etc.) is used to functionally group the test shot according to one or more functional groups. The classifier algorithm used to functionally group the test shot is trained by application of the classifier algorithm to the previous data included in the database. The functional groups correspond to differences in variables that are accounted for in the database. The variables may include data of strong performance metrics, design parameters in one or more test hockey stick(s) used to acquire the previous data, shot parameters in terms of the techniques used when making previous shots to acquire the previous data, or any suitable variables relevant to functionally grouping the database. Classification by functional grouping facilitates analyses which do not rely on isolated variables such as maximum deflection or total impulse. Dynamic variables such as specific properties of the deflection curve or timing of specific impulse events may also provide a basis upon which to define functional groups.

In summary, at step 146, the test principal component score is used to match the test shot with one or more functional group(s). By running the LDA on the test data within the context of the functional groups determined by PCA and LDA of the database, the database may be used to match the test shot with one or more functional groups. The matching is not based directly on identified variables in isolation, such as maximum deflection or total impulse. Rather, dynamic emergent variables based on PCA provide a basis upon which to functionally group the test shot. The dynamic emergent variables may include specific properties of the deflection curve or timing of specific impulse events.

Functional grouping with an LDA classifier prediction may be based on Eq. 1:

$$\hat{y} = \underset{y=1, \ldots, K}{\operatorname{argmin}} \sum_{k=1}^{K} \hat{P}(k \mid x) C(y \mid k) \quad \text{(Eq. 1)}$$

In Eq. 1, $\hat{y}$ is the predicted classification, K is the number of classes, $\hat{P}(k|x)$ is the posterior probability of class k for observation x, and $C(y|k)$ is the cost of classifying an observation as y when its true class is k.

At step 148, a design parameter (e.g. shaft stiffness, blade curve, lie angle, other design parameter, etc.) for a selected hockey stick matched with the test shot is defined. The design parameter is defined with reference to a corresponding design parameter associated with the strong performance metric for the matched functional group in the previous data. The design parameter may be selected with reference to a variety of performance metrics. Puck velocity, total impulse, peak stick deflection, low stick deflection at release, blade-puck contact time, and accuracy, are all suitable performance metrics on which to base an assessment and functional grouping of the test shot.

Where the design parameter selected at step 148 is stiffness, the corresponding design parameter in the previous data will also be stiffness. The stiffness value of the selected stick would be selected to correspond with the stiffness value that was associated with the strong performance in the previous data. Other design parameters of the hockey stick, (e.g. blade curve, lie angle, other design parameter, etc.) may also be design parameters that are selected for the test shot based on the comparison at step 146. The test player's shot style may also be treated as a variable if the database includes data of previous players' shot styles. Each of these features will contribute to the functional grouping of a given test shot once the classifier algorithm has been trained by a database including appropriately defined previous data. The previous data in the database may be defined both in terms of the type(s) of data used as one or more performance metric(s), and in the design feature(s), shot technique(s), or both, which affect one or more of the performance metrics.

Through application of the methods 40 or 140, the test player need not take a test shot under all conditions defined within the database. Test data acquired of a single test shot allows a comparison of shot parameters to all athlete data in the database and matching of a hockey stick design parameter based on the resulting functional grouping.

Alternatively or in addition to matching a design parameter, the test data acquired in either of the methods 40 or 140 may be added as additional empirical data to the database to expand the database. Where the additional empirical data is to be included, the player may in some cases make shots with a greater variety of design parameters in the test hockey stick or other striking tool, with a greater number of shot techniques, or otherwise under broader conditions that would be the case for the test shot and otherwise in accordance with the scope of individual players' data sets used in the database. The additional empirical data may improve the database by adding a greater amount of data to the database and providing further definition of the functional groups defined in the database. However, once the database includes a sufficient number of player shot samples to provide a meaningful reference point for functional grouping of future shot data, the database may be used to match the test player with a hockey stick having a shaft with a stiffness according to one of the three functional groups.

EXAMPLE I

A database as described herein was assembled by collecting data of over 1,000 shots total from 48 athletes taking both slap and wrist shots with sticks of three shaft stiffness values. The shaft stiffness values used are labelled in FIGS. 8, 9, 11, and 12 as flexible (85 flex), stiff (100 flex), and stiffest (110 flex). All data was acquired with the Heatley blade pattern described above in Table 1. Stick deflection, puck-stick contact time, and maximum puck velocity were recorded over the duration of each shot for each athlete using each of the three shaft conditions. Impulse, peak stick deflection, and stick deflection at release were also each calculated.

Figure 8:
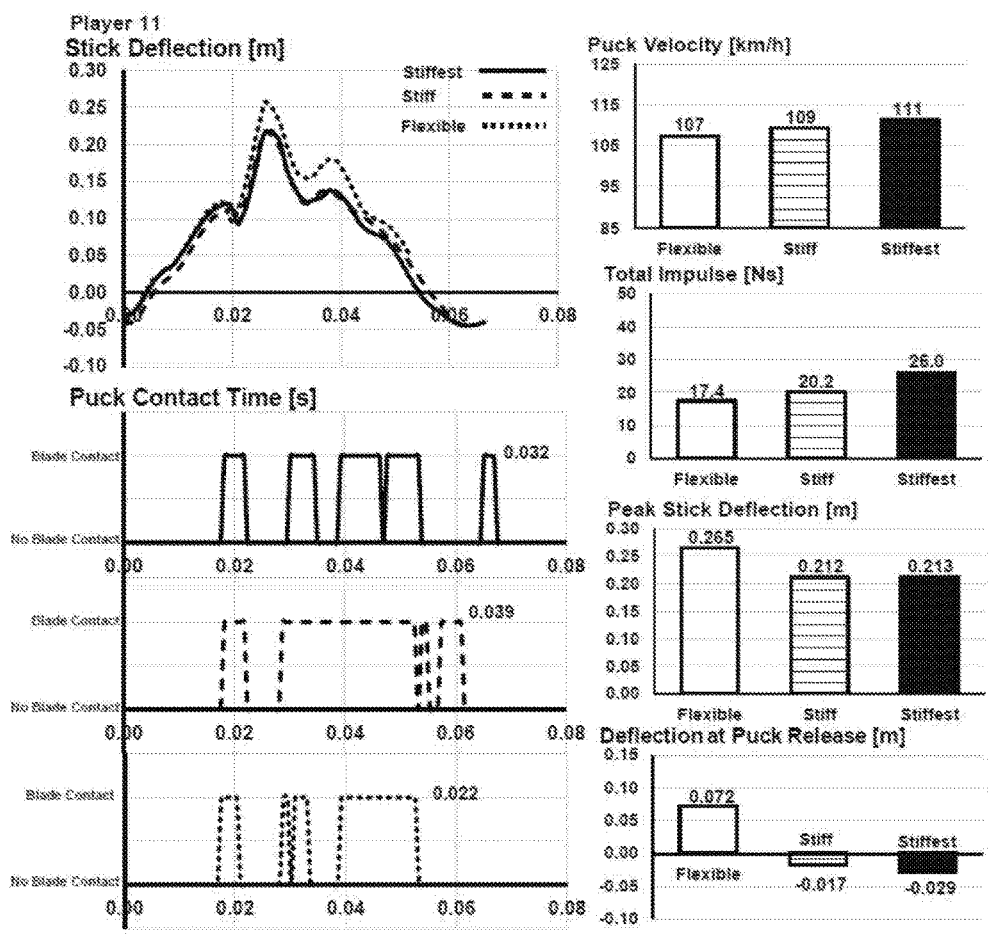
FIG. 8 shows data of a first database player (Player 11) received during three shots with hockey sticks of varying shaft stiffness used as an example database for the method of FIG. 7.
Figure 9:
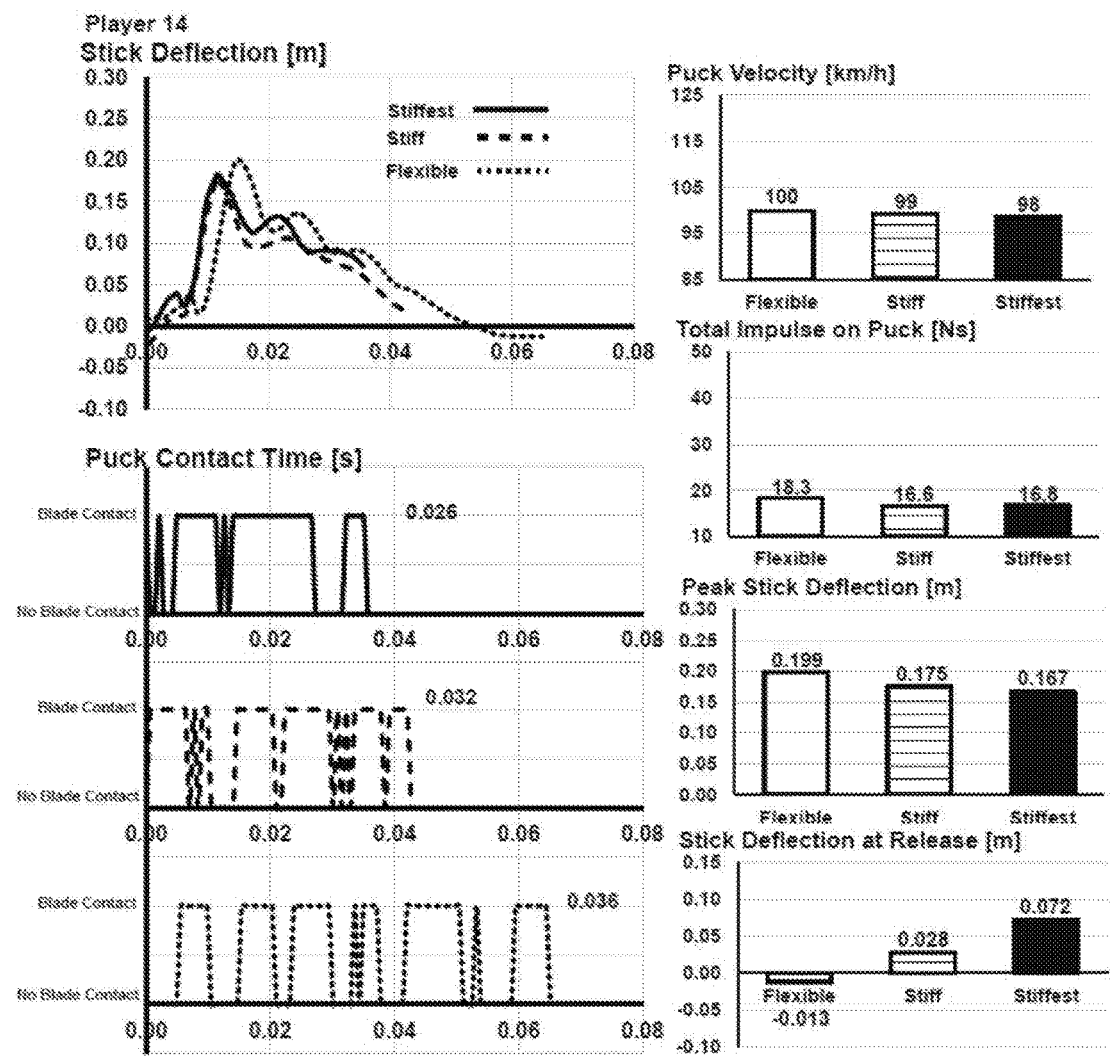
FIG. 9 shows data of a second database player (Player 14) received during three shots with hockey sticks of varying shaft stiffness used as an example database for the method of FIG. 7.

FIGS. 8 and 9 show results of two sample athletes (Player 11 and Player 14) from whom data was acquired with all three shaft stiffness values and included in the database. Player 11 had the strongest results in terms of both puck velocity and impulse with the 110 flex stick. Player 14 had the strongest results in terms of both puck velocity and impulse with the 85 flex stick. These two players show different profiles and are associated with different functional groups based on LDA.

FIG. 8 shows stick deflection over time, puck-stick contact time over time, mean maximum puck velocity, mean impulse, mean peak stick deflection, and mean stick deflection at release at all three shaft stiffness values for Player 11. Player 11 had the strongest puck velocity value, 111 km/h, when shooting with the stiffest stick (110 flex shaft), and the weakest puck velocity value, 107 km/h, when shooting with the flexible stick (85 flex shaft). Player 11 also had the strongest impulse (26.0 Ns) with the stiffest stick and the weakest impulse (17.4 Ns) with the flexible stick.

However, as shown in FIG. 8, not all of the defined values used as performance metrics showed the strongest result for Player 11 with the stiffest stick. Player 11 showed greater peak stick deflection with the flexible stick (0.072 m) compared with the stiffest stick (0.213 m). Player 11 also showed a lower magnitude of deflection at puck release with the stiff stick (−0.017) compared with the stiffest stick (−0.029). Finally, Player 11 showed a greater total puck contact time with the stiff stick (0.039 sec) than with the stiffest stick (0.032 sec).

The greatest performance with the stiffest stick was observed despite the peak stick deflection being greater with the flexible stick, the deflection at puck release being lower than with the stiff stick, and the total contact time being lower than with the stiff stick. This outcome illustrates that the mean puck velocity and mean impulse are not determined by a single defined variable, and that strong performance according to some metrics can result from a stick that has lower scores in other metrics.

FIG. 9 shows stick deflection over time, puck-stick contact over time, mean maximum puck velocity, mean impulse, mean peak stick deflection, and mean stick deflection at release at all three shaft stiffness values for Player 14. Player 14 had the strongest puck velocity, 100 km/h, when shooting with the flexible stick, and the weakest puck velocity, 98 km/h, when shooting with the stiffest stick. Player 14's stronger performance with the flexible stick may be due to contributions from a greater peak stick deflection (0.199 m), greater impulse applied to the puck (18.3 Ns), and greatest blade-puck contact time (0.036), with the flexible stick. Additionally, the mean stick deflection at puck release was much lower in the flexible stick than for the stiffest stick, being −0.013, or very close to zero. Unlike the case in FIG. 8 with Player 11, FIG. 9 shows that Player 14 performed most strongly with the flexible stick across all defined values used as performance metrics.

As can be seen from FIGS. 8 and 9, maximum puck velocities are achieved with sticks of different stiffness for different players. The differences may depend on how individual players load the stick during a shot. Stick deflection over time, puck-stick contact over time, mean maximum puck velocity, mean impulse, mean peak stick deflection, and mean stick deflection at release data relating to a large number of athletes are included in the database, with the data in FIGS. 8 and 9 being examples of the previous data included in the database. Other less discrete variables, such as the shape of the stick deflection curve, patterns in the contact time profile, or correlation between the stick deflection curve and the contact time profile, are also available in the database and may be applied to define functional groups.

The database shows similarities between athletes who performed best with the flexible stick, between athletes who performed best with the stiff stick, and between athletes who performed best with the stiffest stick. To classify the athletes according to functional groups, PCA was first conducted on all the data in the database. The PCA reconstructed the data in principal component space, where each principal component is a combination of the measured variables that indicates portions of test data that result in the highest variability across data of all shots. That is, the test data includes data of stick deflection over time, puck-stick contact over time, mean maximum puck velocity, mean impulse, mean peak stick deflection, and mean stick deflection at release. The principal components that account for a sufficient amount of variability in the data are retained for classifying the athletes using LDA. As above, a number of principal components sufficient to account for 90 to 95% of the variability in the database may be applied, which in some cases could include 12 to 14 principal components.

Figure 10:
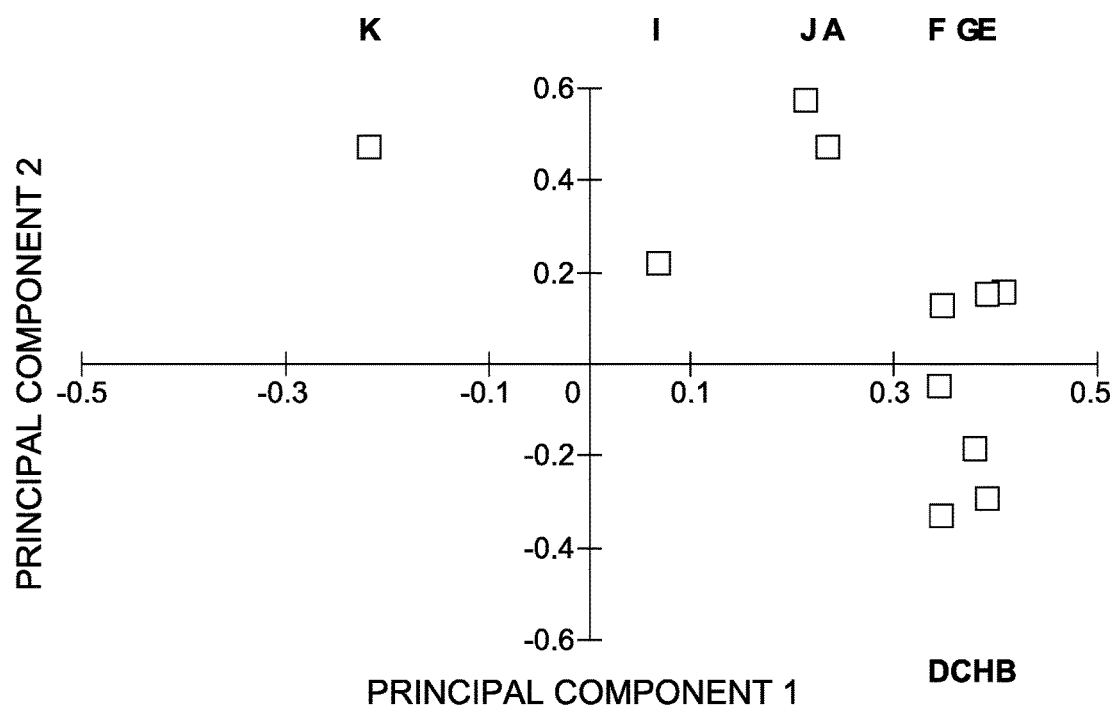
FIG. 10 shows a bi-plot of the principal component coefficients for each variable that contributes to the first two principal components relevant to selecting a shaft stiffness.

FIG. 10 shows a bi-plot of the principal component coefficients for each variable used to define the principal component 1 (shown on the x-axis) and principal component 2 (shown on the y-axis) based on the database. The PCA showed that the principal components describing the most variation are determined by multiple variables of the shot and relationships between these variables. The variables shown and their values in FIG. 10 are listed below in Table 2 ("PC" in Table 2 means principal component). The direction and length of each variable indicate the magnitude of each variable's contribution to principal component 1 and to principal component 2.

TABLE 2

Data and Variable Legend of in FIG. 10

| Variable | PC 1 | PC 2 |
|---|---|---|
| A - Puck Velocity [km/h] | 0.219884 | 0.447019 |
| B - Total Contact Time [s] | 0.368602 | −0.27505 |
| C - Contact Time before Peak Deflection [s] | 0.323366 | −0.04294 |
| D - Contact Time after Peak Deflection [s] | 0.328265 | −0.31228 |
| E - Total Impulse [Ns] | 0.383938 | 0.149031 |
| F - Impulse before Peak Deflection [Ns] | 0.327664 | 0.120769 |
| G - Impulse after Peak Deflection [Ns] | 0.36758 | 0.145196 |
| H - Shot Time [s] | 0.357624 | −0.17084 |
| I - Number of Separations | 0.064002 | 0.206578 |
| J - Peak Deflection [cm] | 0.198728 | 0.545605 |
| K - Deflection at Release [cm] | −0.20515 | 0.444677 |

The number of separations (value I on the graph) is in reference to separations between the blade 24 and the test puck 12 during the shot. The total impulse is a derived value calculated using deflection, stick stiffness and puck-blade contact time.

Where a particular variable has a greater contribution to either of principal component 1 or principal component 2, it will have a correspondingly higher value on the x or y axes, respectively, of FIG. 10. As shown in FIG. 10 and by bolding in Table 2, contact time, total impulse, impulse after peak deflection, shot time, and deflection at release variables each contribute heavily to principal component 1. Shot speed, deflection at peak deflection, and puck release variables each contribute heavily to principal component 2. Number of separations and total Impulse also contribute to principal component 2, but to a lower degree. Each of these variables showed high variability between shots with different sticks or between shots by different players. In addition to the two principal components shown in Table 2 and FIG. 10, eleven additional principal components defined in terms of the same variables were measured and their contributions to variability defined. The data of these additional principal components are provided in Table 3 (no bi-plot of these other principal components is shown in a figure):

TABLE 3

Principal components not shown in FIG. 10

| Variable | PC 3 | PC 4 | PC 5 | PC 6 | PC 7 |
|---|---|---|---|---|---|
| A [km/h] | 0.033639 | −0.15557 | 0.804077 | 0.264037 | 0.029787 |
| B [s] | 0.116494 | −0.12389 | −0.02407 | 0.128759 | −0.19346 |
| C [s] | −0.21181 | 0.547358 | 0.002911 | 0.35188 | −0.40253 |
| D [s] | 0.214778 | −0.33541 | −0.03273 | 0.03323 | −0.09818 |
| E [Ns] | 0.190053 | 0.085305 | −0.11578 | −0.16867 | 0.35049 |
| F [Ns] | −0.08435 | 0.58147 | −0.05475 | −0.20876 | 0.199058 |
| G [Ns] | 0.278515 | −0.11756 | −0.1281 | −0.13609 | 0.374739 |
| H [s] | −0.1893 | −0.25856 | −0.19897 | 0.415196 | 0.021411 |
| I [n] | −0.77499 | −0.25158 | −0.18618 | 0.08401 | 0.312 |
| J [cm] | −0.03607 | −0.23627 | −0.26077 | −0.3778 | −0.61974 |
| K [cm] | 0.368445 | 0.056381 | −0.4204 | 0.613229 | 0.072373 |
| Variable | PC 8 | PC 8 | PC 10 | PC 11 | |
| A [km/h] | −0.09318 | −0.02576 | 0.001067 | −5.2E−07 | |
| B [s] | −0.00744 | −0.38558 | −0.74582 | −0.00018 | |
| C [s] | 0.465111 | −0.00852 | 0.216485 | 5.23E−05 | |
| D [s] | −0.17574 | −0.44341 | 0.629908 | 0.000147 | |
| E [Ns] | 0.165344 | 0.060852 | 0.000718 | 0.768925 | |
| F [Ns] | −0.61093 | −0.13794 | −0.00081 | −0.23316 | |
| G [Ns] | 0.452843 | 0.132631 | 0.001639 | −0.59531 | |
| H [s] | −0.32561 | 0.649406 | −0.00681 | 1.2E−06 | |
| I [n] | 0.115852 | −0.36987 | 0.00583 | 6.32E−07 | |
| J [cm] | −0.07195 | 0.07548 | −0.00374 | 3.16E−06 | |
| K [cm] | −0.11743 | −0.22233 | −0.00042 | −7.8E−07 | |

After the PCA transformation, LDA was applied to functionally group the shots included in the database into three groups and to train a classifier algorithm to be used for comparing future test data to the database. The three groups correspond to the three shaft stiffness values used to acquire the data included in the database as shown in FIGS. 8 and 9, with each group being defined by which of the three shaft stiffness values resulted in the strongest performance in terms of puck velocity. To assess whether subsequent test data is within one of the three groups, test data is transformed into the existing principal component space and entered into the LDA classifier to compare with the principal component score of the test data with the database in principal component space. The PCA and LDA analyses do not rely only on isolated variables such as maximum deflection or total impulse. Rather, combinations of these variables and the relationships between the variables are characterized by the PCA and LDA. Dynamic variables such as specific properties of the deflection curve or timing of specific impulse events may provide a basis upon which to define functional groups.

Figure 11:
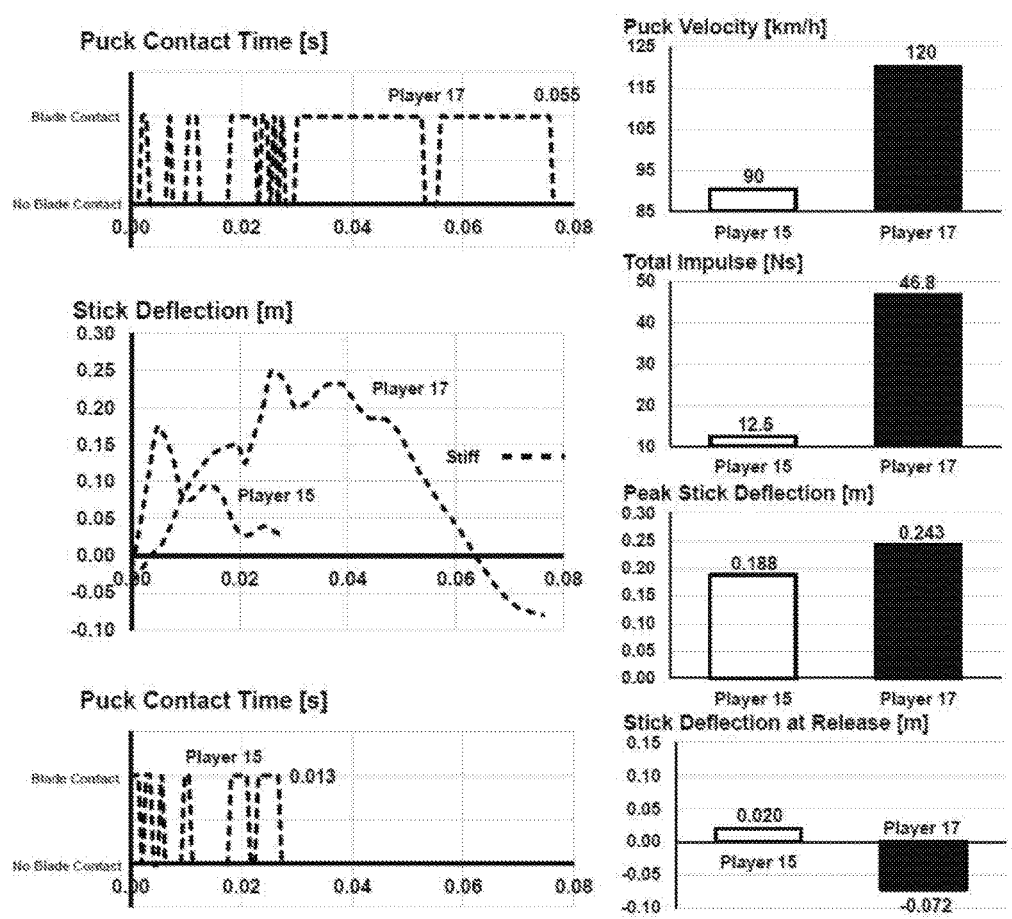
FIG. 11 shows data of two test players (Player 15 and Player 17) received during a single shot per player with a hockey stick of known shaft stiffness.

FIG. 11 is data of two players, Player 15 and Player 17, being applied as test players to the method 140 and the database including the data shown in FIGS. 8 and 9. In FIG. 11, data is shown of a test shot by each player using the test hockey stick similar to the test hockey stick 20 with a stiff shaft (100 flex) in conjunction with a data acquisition system similar to the data acquisition system 30 as shown in FIG. 1. For each of Players 15 and 17, the same data as included for each shaft stiffness value in the database are shown in curves of stick deflection vs time and contact vs time, and mean values of puck velocity, total impulse, peak stick deflection, and stick deflection at release, are shown. However, each of Players 15 and 17 used a single test hockey stick 20.

As shown in the data of FIG. 11, Players 15 and 17 have very different shot characteristics. Player 17 showed a greater puck velocity (120 km/h) than Player 15 (90 km/h). Player 15 also has less stick deflection, less impulse, and a shorter contact time than Player 17. However, Player 15 also showed a lower stick deflection at puck release than Player 17.

Using the PCA and LDA with reference to the database, Player 15 was found to have similar shot characteristics to Player 14 in the database and was grouped into the same functional grouping. Player 15 was matched with the flexible (85 flex) stick.

In contrast to Player 15, Player 17 is able to bend the stick to a greater amount, has a long total contact time, greater mean impulse, and a large stick deflection at puck release. Using the PCA and LDA with reference to the database, Player 17 was found to have similar shot characteristics to Player 11 in the database and was grouped into the same functional grouping. Player 17 was matched with the stiffest (110 flex) stick.

Figure 12:
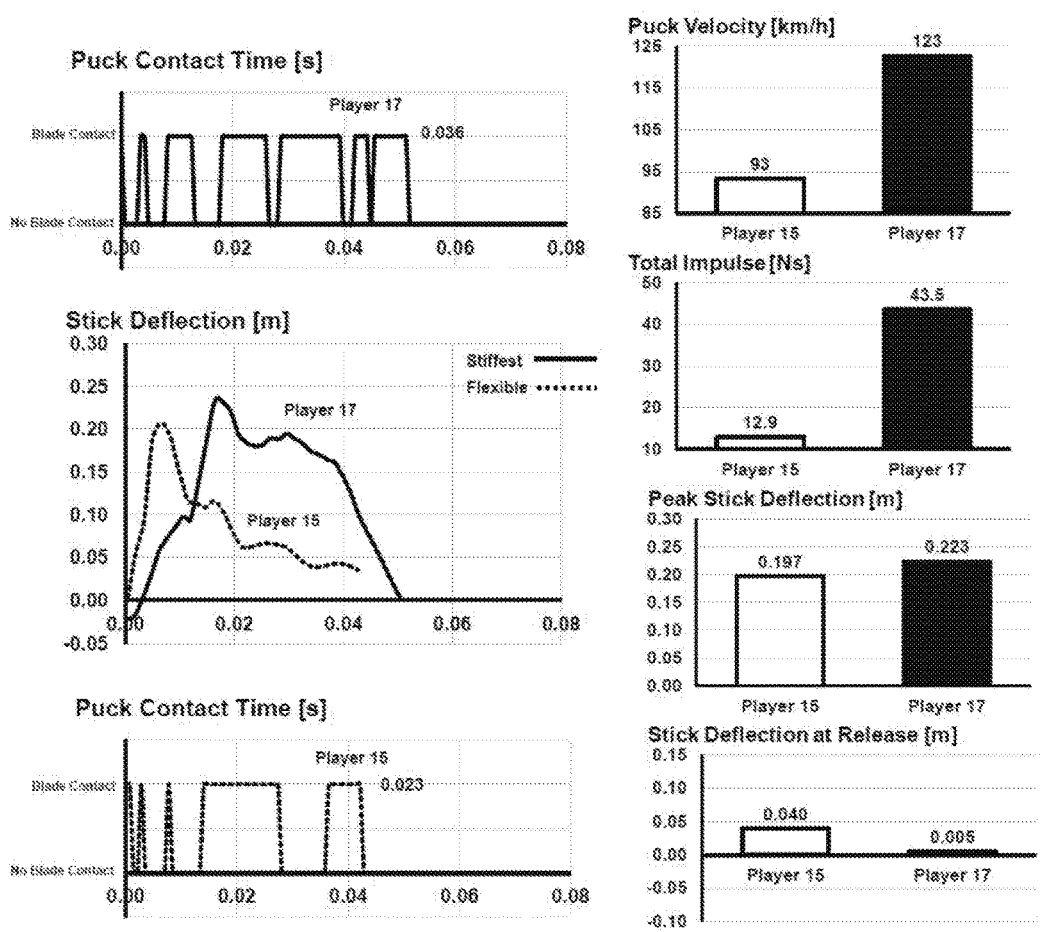
FIG. 12 shows data of the two test players of FIG. 11 received during a single shot per player with a hockey stick having a shaft stiffness selected for each player.

FIG. 12 shows each of Players 15 and 17 shooting with the sticks that they were respectively matched with based on the data shown in FIG. 11. A comparison of values of strong performance metrics observed for Player 15 using the 100 flex test hockey stick 20, compared with the matched 85 flex stick, is shown in Table 4:

TABLE 4

Summary of Player 15 results

| Performance Metric | Test (100 flex) | Matched (85 flex) | Improved? |
|---|---|---|---|
| Puck Velocity (km/h) | 90 | 93 | Yes |
| Contact time (s) | 0.013 | 0.023 | Yes |
| Peak Deflection (m) | 0.188 | 0.197 | Yes |
| Impulse (Ns) | 12.5 | 12.9 | Yes |
| Deflection at Release (m) | 0.020 | 0.040 | No |

Similarly, a comparison of values of strong performance metrics observed for Player 17 using the 100 flex test hockey stick 20, compared with the matched 110 flex stick, is shown in Table 5:

TABLE 5

Summary of Player 17 results

| Performance Metric | Test (100 flex) | Matched (110 flex) | Improved? |
|---|---|---|---|
| Puck Velocity (km/h) | 120 | 123 | Yes |
| Contact time (s) | 0.055 | 0.036 | No |
| Peak Deflection (m) | 0.243 | 0.223 | No |
| Impulse (Ns) | 46.8 | 43.5 | No |
| Deflection at Release (m) | −0.072 | 0.005 | Yes |

As shown in FIGS. 11 and 12, and Tables 4 and 5, while puck velocity improved for both players, the remaining performance metrics were not consistently improved. By otherwise training the classifier algorithm based on the same database, selection of design parameters to correlate with performance metrics other than puck velocity may be affected. Training the algorithm to maximize impulse, minimize deflection at release, define and maximize accuracy, or to otherwise optimize the shot with reference to design parameters, may result in recommendations based on other design parameters such as blade features, or may result in recommending that a player alter their shot technique, or combinations thereof. Thus, application of functional grouping increases the options for optimizing player performance and allows multiple variables, and combinations of variables which may not be realistically predictable in theory, to drive matching of a player with striking equipment.

EXAMPLE II

Figure 15:
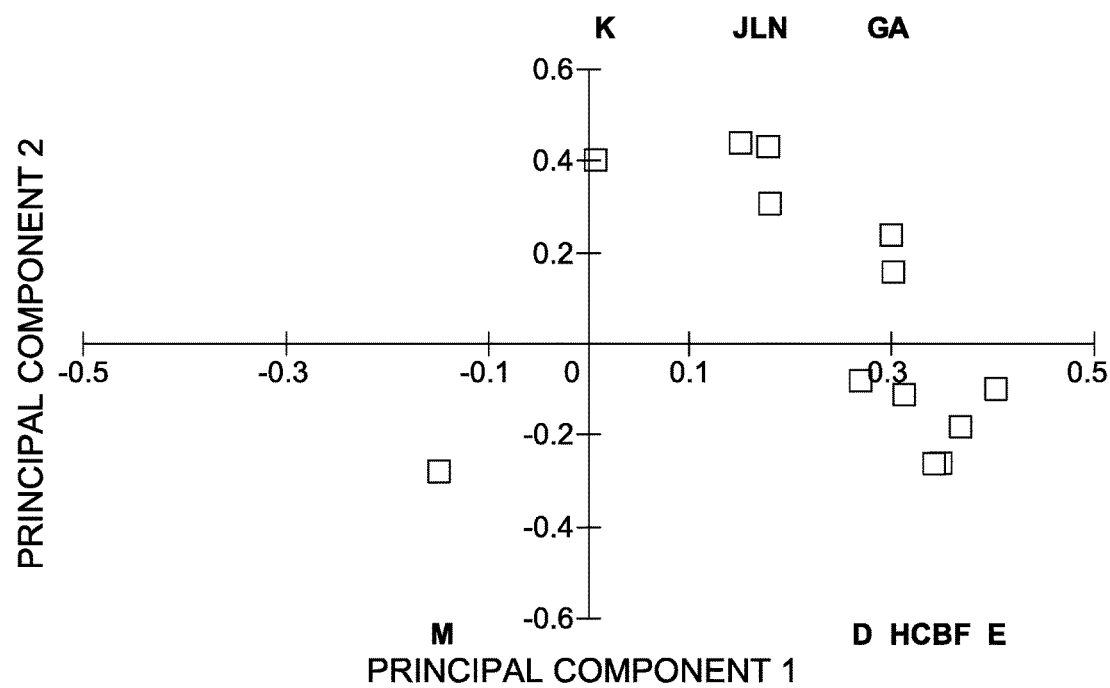
FIG. 15 shows a bi-plot of the principal component coefficients for each variable that contributes to the first two principal components relevant to selecting a blade curve or lie angle.

A database with the principle components contributions shown in FIG. 15 was prepared with data from over 2,000 shots total from 68 athletes with data of shots with different blade designs. Shot data was acquired with Duchene, Datsyuk, Phaneuf, and Crosby blades as described above in Table 1. All blades used in this example are from the Reebok 20K. All shafts used on a test hockey stick had a stiffness of 100 flex.

These four blade patterns provide systematic differences in lie angle and blade curvature. The Phaneuf blade pattern provides a heel curve and the Crosby P87A blade pattern provides a mid-heel curve (treated as mid in this example). The Duchene blade pattern provides a low lie angle and the Datsyuk blade pattern provides a high lie angle.

Additional data with variable other blade curves, lie angles, or other aspects of the blade patterns may be added and the LDA classifier algorithm used in this specific example will be trained to identify and classify data into functional groups based on blade curve, lie angle, or other aspects of the blade pattern.

Samples of data included in the database applied in Example II are provided below with reference to FIGS. 13 and 14, and to Player 18, whose data is summarized below but not provided in a figure. Each of these datasets was based on 40 shots with variable indicated in terms of blade curve and lie angle. As above, all shots were with a test hockey stick 20 having a shaft 22 with a stiffness of 100 flex.

Figure 13:
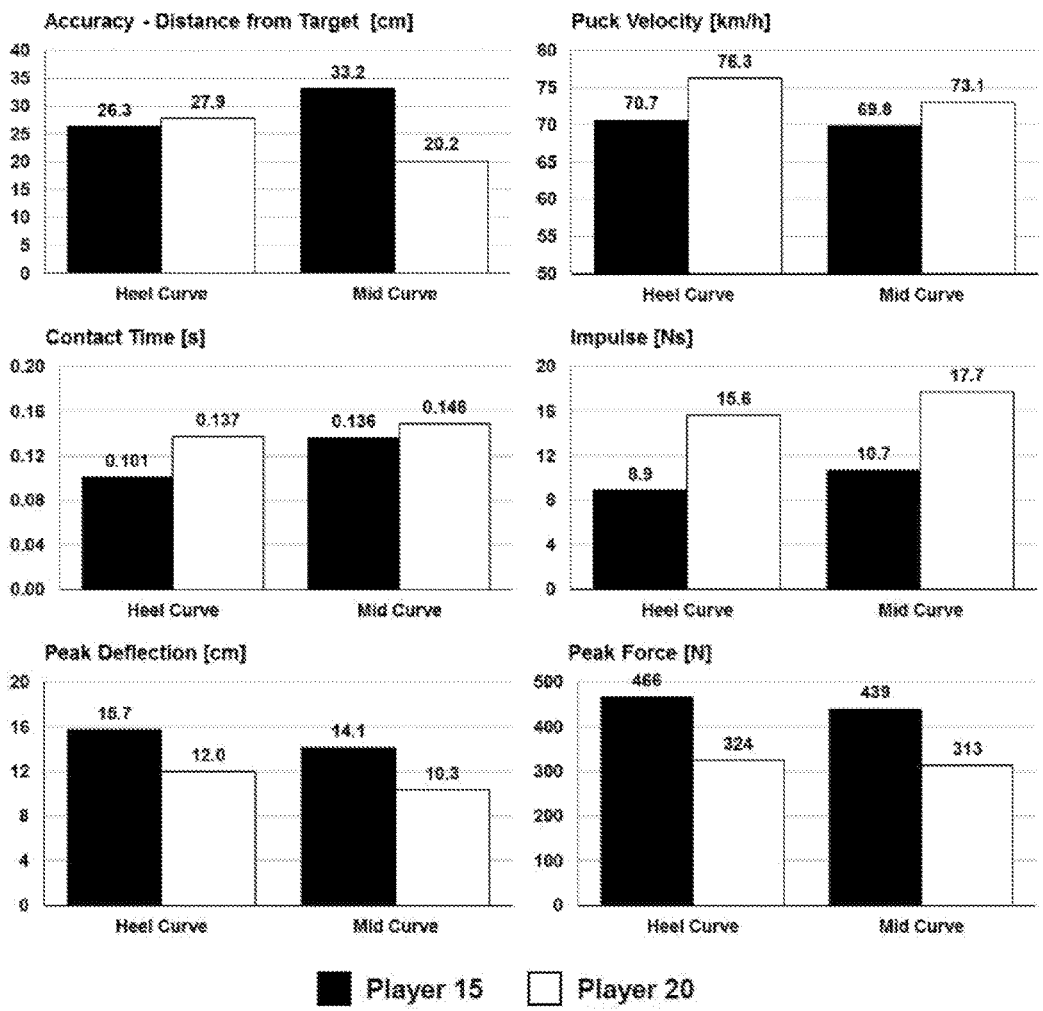
FIG. 13 shows average shot data of two test players (Player 15 and Player 20) received during multiple shots, each of the shots applying one of two hockey sticks of known blade curve.

FIG. 13 shows results of one sample athlete (Player 15) from whom data was acquired with both curve values (Phaneuf blade pattern provides the heel curve data and the Crosby P87A blade pattern provides the mid curve data). Player 15 had the strongest results in terms of both accuracy and peak force with the heel curve. T FIG. 14 shows results of one sample athlete (Player 10) from whom data was acquired with both lie angle values (Datsyuk blade pattern provides the high angle data and the Duchene blade pattern provides the low angle data). Player 10 had the strongest results in terms of both accuracy and peak force with the low lie angle.

Figure 14:
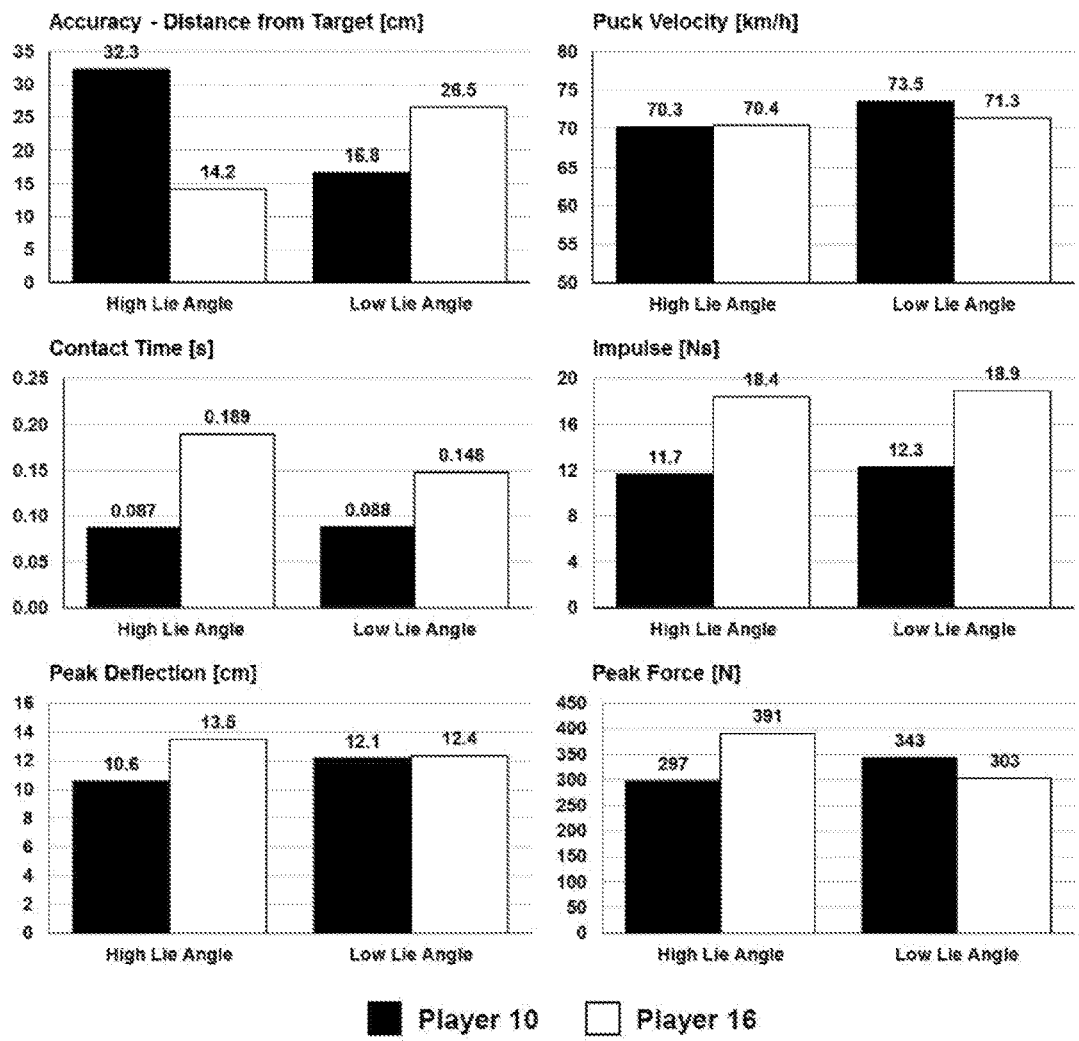
FIG. 14 shows average shot data of two test players (Player 10 and Player 16) received during multiple shots, each of the shots applying one of two hockey sticks of known lie angle.

In addition to the data shown in FIGS. 13 and 14, data from an additional player (Player 18), is provided as further example data used in the database of Example II. With the heel curve, Player 18 had average values of 16.6 cm from target, 0.202 s contact time, 13.5 cm peak deflection, 77.3 km/h puck velocity, 20.6 Ns impulse, and 391 N peak force, over Player 18's 40 shots included in the database.

As in Example I with respect to velocity, PCA and LDA was applied to the database. As in Example I, a number of principal components sufficient to account for 90 to 95% of the variability in the database may be applied, which in some cases could include 12 to 14 principal components.

FIG. 15 shows a bi-plot of the principal component coefficients for each variable used to define the principal component 1 (shown on the x-axis) and principal component 2 (shown on the y-axis) based on the database. The PCA showed that the principal components describing the most variation are determined by multiple variables of the shot and relationships between these variables. The variables shown and their values in FIG. 15 are listed below in Table 6 ("PC" in Table 6 means principal component). The direction and length of each variable indicate the magnitude of each variable's contribution to principal component 1 and to principal component 2.

TABLE 6

Data and Variable Legend of in FIG. 15

| Variable | PC 1 | PC 2 |
|---|---|---|
| A - Puck Velocity [km/h] | 0.300182 | 0.236448 |
| B - Total Contact Time [s] | 0.351206 | −0.26854 |
| C - Contact Time before Peak Deflection [s] | 0.343383 | −0.27004 |
| D - Contact Time after Peak Deflection [s] | 0.270469 | −0.08775 |
| E - Total Impulse [Ns] | 0.404222 | −0.10183 |
| F - Impulse before Peak Deflection [Ns] | 0.368074 | −0.18892 |
| G - Impulse after Peak Deflection [Ns] | 0.303002 | 0.151351 |
| H - Shot Time [s] | 0.311956 | −0.11664 |
| J - Peak Deflection [cm] | 0.14964 | 0.435338 |
| K - Deflection at Release [cm] | 0.008728 | 0.401313 |
| L - Peak Force [N] | 0.17709 | 0.428396 |
| M - Average Distance from Target [cm] | −0.14664 | −0.28915 |
| N - Accuracy [%] | 0.179294 | 0.301794 |

Where a particular variable has a greater contribution to either of principal component 1 or principal component 2, it will have a correspondingly higher value on the x or y axes, respectively, of FIG. 15. As shown in FIG. 15 and by bolding in Table 5, total contact time, contact time before peak deflection, total impulse, and impulse before peak deflection each contribute heavily to principal component 1. Puck velocity, contact time after peak deflection, impulse after peak deflection, and shot time also contribute to principal component 1, but to a lower degree. In addition to the two principal components shown in Table 5 and FIG. 15, eleven additional principal components defined in terms of the same variables were measured and their contributions to variability defined. The data of these additional principal components are provided in Table 7 (no bi-plot of these other principal components is shown in a figure):

TABLE 7

Principal components not shown in FIG. 15

| Variable | PC 3 | PC 4 | PC 5 | PC 6 | PC 7 | PC 8 |
|---|---|---|---|---|---|---|
| A [km/h] | 0.259083 | −0.43191 | 0.081626 | 0.030915 | 0.013982 | −0.04565 |
| B [s] | −0.0622 | 0.188545 | 0.125119 | 0.017318 | −0.04447 | −0.46305 |
| C [s] | −0.0709 | 0.235431 | 0.116857 | 0.012389 | −0.04066 | −0.46517 |
| D [s] | 0.116041 | −0.67196 | 0.164695 | 0.080375 | −0.0846 | −0.17101 |
| E [Ns] | 0.193391 | −0.02317 | −0.25151 | −0.27268 | −0.10358 | 0.295943 |
| F [Ns] | 0.140098 | 0.113051 | −0.31651 | −0.32339 | −0.12134 | 0.344122 |
| G [Ns] | −0.0984 | 0.11222 | −0.57391 | 0.639805 | 0.279193 | −0.0228 |
| H [s] | −0.13502 | 0.272706 | 0.57646 | 0.109818 | 0.197212 | 0.437923 |
| J [cm] | 0.182424 | 0.149487 | 0.216628 | 0.057017 | 0.194727 | 0.025785 |
| K [cm] | 0.330182 | 0.354387 | −0.07921 | −0.22329 | −0.36193 | −0.29618 |
| L [N] | 0.191985 | 0.07663 | 0.197399 | 0.01438 | 0.147863 | 0.013246 |
| M [cm] | 0.578246 | 0.121505 | 0.126121 | 0.553954 | −0.4164 | 0.167216 |
| N [%] | −0.55861 | −0.04573 | 0.060931 | 0.177791 | −0.69467 | 0.151823 |

| Variable | PC 9 | PC 10 | PC 11 | PC 12 | PC 13 |
|---|---|---|---|---|---|
| A [km/h] | 0.16106 | −0.70645 | −0.15295 | −0.19875 | −0.05006 |
| B [s] | 0.144122 | 0.002004 | −0.01857 | 0.176028 | −0.6933 |
| C [s] | 0.170094 | −0.02687 | −0.0269 | −0.16914 | 0.676671 |
| D [s] | −0.40452 | 0.460729 | 0.079986 | −0.00853 | 0.042155 |
| E [Ns] | 0.097056 | −0.02192 | −0.04026 | 0.713161 | 0.179604 |
| F [Ns] | 0.048994 | 0.197633 | 0.004467 | −0.62621 | −0.1578 |
| G [Ns] | −0.2081 | −0.01519 | 0.047616 | 0.002952 | 0.000117 |
| H [s] | −0.42802 | −0.18623 | 0.059631 | 9.30E−05 | 3.96E−05 |
| J [cm] | 0.18247 | 0.401703 | −0.6701 | −0.00153 | −0.00107 |
| K [cm] | −0.5614 | −0.10626 | 0.053844 | 0.007456 | 0.000332 |
| L [N] | 0.365513 | 0.196906 | 0.713299 | −0.00163 | 0.002077 |
| M [cm] | 0.143261 | 0.032919 | −0.00398 | −0.00324 | −0.00033 |
| N [%] | 0.140712 | 0.031037 | −0.03044 | −0.0028 | −0.00036 |

As shown in FIG. 15 and Tables 6 and 7, shot speed, deflection at peak deflection, and puck release, and variables each contribute heavily to principal component 2. Contact time before peak deflection, and puck velocity also contribute to principal component 2, but to a lower degree. Each of these variables showed high variability between shots with different sticks or between shots by different players.

After the PCA transformation, LDA was applied to functionally group the shots included in the database into two groups for blade curve, and another two groups for lie angle, and to train a classifier algorithm to be used for comparing future test data to the database. The four groups correspond to the two blade curve values and the two lie angle values used to acquire the data included in the database as shown in FIG. 13 (blade curve) and in FIG. 14 (lie angle).

Each group is defined by which of the two blade curve values or the two lie angle values resulted in the strongest performance in terms of accuracy. To assess whether subsequent test data is within one of the two blade curve groups or the two lie angle groups, test data is transformed into the existing principal component space and entered into the LDA classifier to compare the principal component score of the test data with the database in principal component space. As with puck velocity in Example I, the PCA and LDA analyses do not rely only on isolated variables such as total impulse or peak deflection. Rather, combinations of these variables and the relationships between the variables are characterized by the PCA and LDA. Dynamic variables such as timing of specific impulse events may provide a basis upon which to define functional groups.

Figure 16:
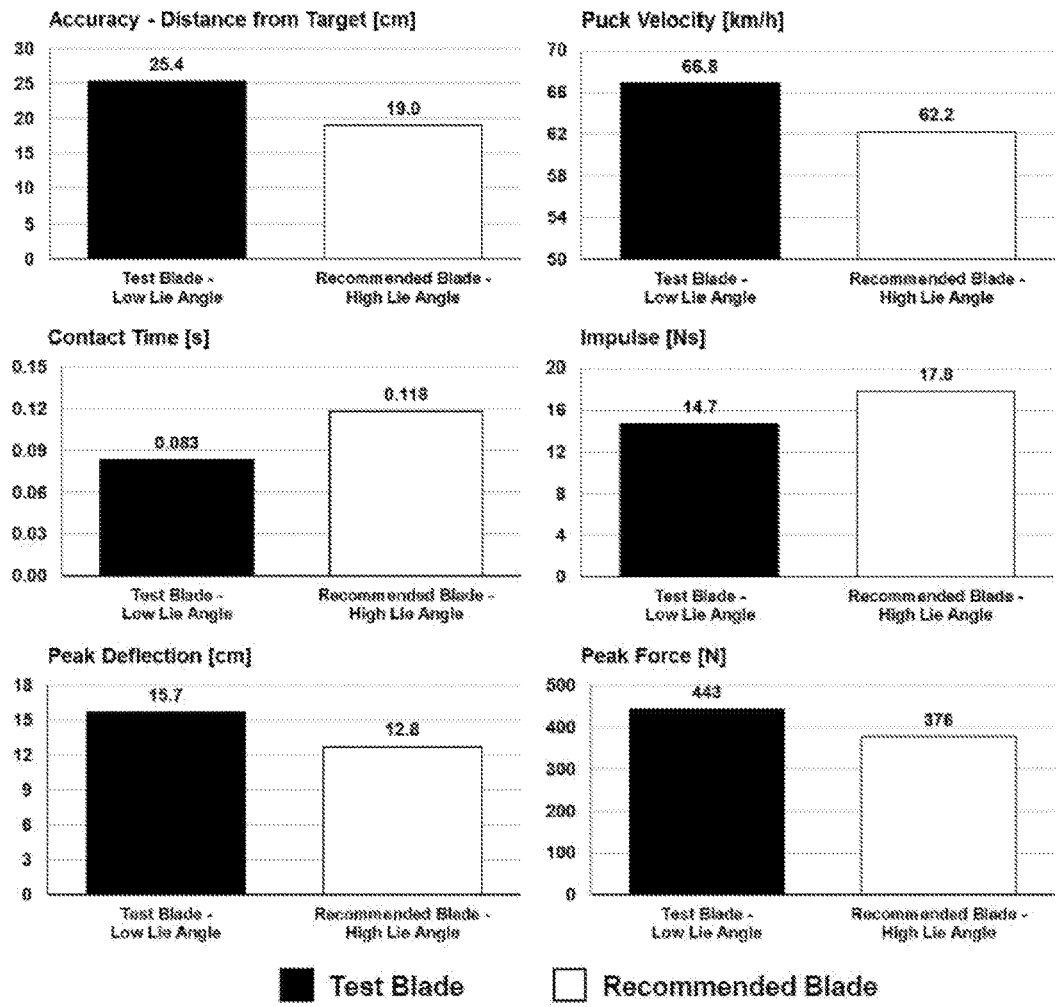
FIG. 16 shows data of a test player (Player 12) received during a single shot with a test hockey stick and with a hockey stick having a lie angle selected for the player.

FIG. 16 is data of Player 12 as a test player for the method 140 and the database including the data shown in FIGS. 13 and 14 with the principal component contributions shown in FIG. 15 and Tables 6 and 7. FIG. 16 shows Player 12 shooting with a test hockey stick 20 with a selected hockey stick having a lie angle selected for Player 12 based on a principal component analysis applying the data shown in FIG. 15 and summarized in tables 6 and 7. Both the test hockey stick 20 and the selected hockey stick had a shaft stiffness of 100 flex. The test hockey stick 20 included a blade 24 having the Duchene blade pattern, corresponding to a low lie angle. A second test shot of the two test shots included a test hockey stick 20 with a blade 24 having a Datsyuk blade pattern, corresponding to a high lie angle.

A comparison of values of strong performance metrics observed for Player 12 shows improvement in accuracy, as shown in Table 8:

TABLE 8

Summary of Player 12 results

| Performance Metric | Datsyuk (Test; low) | Matched (Duchene; high) | Improved? |
|---|---|---|---|
| Accuracy [cm from target] | 25.4 | 19.0 | Yes |
| Puck Velocity [km/h] | 66.8 | 62.2 | No |

As shown in FIG. 16 and Table 18, while shot accuracy improved, shot velocity, the metric of Example I, decreased with the matched hockey stick. The approaches of Example I and of Example II may be combined to match a blade pattern for accuracy and a shaft stiffness for velocity. The player may take shots with different test hockey sticks sequentially to provide separate test data for matching the player with a functional group to identify a design parameter of the hockey stick to improve shot velocity, accuracy, or both.

A test with a test hockey stick 20 with a blade 24 having either the Phaneuf blade pattern (corresponding to a heel curve) or a the Crosby P87A blade pattern, (corresponding to a mid curve blade—"mid-heel" in Table 1) may also be carried out with results similar in nature to the data shown in FIG. 16. With such an approach, a player may be matched for accuracy based on blade curve using such a system.

EXAMPLES ONLY

In the preceding description, for purposes of explanation, numerous details are set forth in order to provide a thorough understanding of the embodiments. However, it will be apparent to one skilled in the art that these specific details are not required.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

What is claimed is:

1. A method of matching an athlete with a selected striking tool comprising:
   receiving test data resulting from the athlete hitting a target object with a test striking tool for launching the target object;
   transforming the test data for defining a test functional group score;
   comparing the test functional group score with a database for matching the test functional group score with matched previous data having a similar functional group score to the test functional group score; and
   recommending a design parameter value of the selected striking tool with reference to a corresponding design parameter value associated with a strong performance metric in the matched previous data.

2. The method of claim 1 wherein:
   transforming the test data comprises transforming the test data into a principal component space defined by the database;
   the test functional group score comprises a principal component score;
   comparing the test functional group score with the database comprises comparing the test principal component score with the database in the principal component space; and
   the matched previous data comprises data having a similar principal component score to the test principal component score.

3. The method of claim 2 further comprising processing at least a portion of the test data to a derived variable and wherein transforming the test data into the principal component space comprises transforming the derived variable.

4. The method of claim 1 wherein the target object comprises a test puck and the test striking tool comprises a test hockey stick.

5. The method of claim 4 wherein:
   transforming the test data comprises transforming the test data into a principal component space defined by the database;
   the test functional group score comprises a principal component score;
   comparing the test functional group score with the database comprises comparing the test principal component score with the database in the principal component space; and
   the matched previous data comprises data having a similar principal component score to the test principal component score.

6. The method of claim 5 further comprising processing at least a portion of the test data to a derived variable and wherein transforming the test data into the principal component space comprises transforming the derived variable.

7. The method of claim 6 wherein:
   the test data comprises stick deflection data;
   a shaft of the test hockey stick has a known stiffness value; and
   processing at least a portion of the test data to the derived variable comprises processing the stick deflection data and the known stiffness value to provide impulse on the puck.

8. The method of claim 4 wherein the test data comprises puck velocity, the design parameter comprises shaft stiffness, and the strong performance metric comprises puck velocity.

9. The method of claim 4 wherein the test data comprises accuracy data, the design parameter comprises a feature of a blade pattern, and the strong performance metric comprises accuracy.

10. The method of claim 9 wherein the accuracy data comprises distance from a target.

11. The method of claim 9 wherein the feature comprises a blade curve.

12. The method of claim 9 wherein the feature comprises a lie angle.

13. A system for matching an athlete with a selected striking tool comprising:
   a data acquisition module for acquiring test data of the athlete hitting a target object with a test striking tool for launching the target object;
   a computer readable processor in communication with the data acquisition module for receiving the test data and having instructions encoded thereon for receiving the test data;
   transforming the test data for defining a test functional group score;
   comparing the test functional group score with a database, wherein the database includes previous test data and at least one defined functional group, for matching the test functional group score with matched previous data in a defined functional group having a similar functional group score to the test functional group score; and recommending a design parameter value of the selected striking tool with reference to a corresponding design parameter value associated with a strong performance metric in the matched previous data; and a computer readable medium in communication with and accessible by the computer readable processor, the computer readable medium having the database stored thereon for access by the computer readable processor.

14. The system of claim 13 wherein the data acquisition module comprises an optical data acquisition module for receiving test data comprising a velocity of the target object.

15. The system of claim 13 wherein the data acquisition module comprises an optical data acquisition module for receiving test data comprising a shaft deflection of the test striking tool.

16. The system of claim 13 wherein the data acquisition module comprises force sensors located on a striking surface of the test striking tool for receiving test data of contact time, contact location, contact force or combinations thereof.

17. The system of claim 13 wherein the data acquisition module comprises conducting material located on a striking surface of the test striking tool and on the target object for receiving test data of contact.

18. The system of claim 13 wherein the data acquisition module comprises strain sensors located on a shaft of the test striking tool for receiving test data of shaft deflection.

19. The system of claim 13 wherein the data acquisition module comprises an inertial sensor located on the target object for receiving test data of target velocity.

20. The system of claim 13 wherein the target object comprises a test puck and the test striking tool comprises a test hockey stick.

21. A non-transitory computer readable medium having instructions encoded thereon for receiving test data resulting from an athlete hitting a target object with a test striking tool for launching the target object;

transforming the test data for defining a test functional group score;

comparing the test functional group score with a database for matching the test functional group score with matched previous data having a similar functional group score to the test functional group score; and recommending a design parameter value of the selected striking tool with reference to a corresponding design parameter value associated with a strong performance metric in the matched previous data.

* * * * *